(12) United States Patent
Shuros et al.

(10) Patent No.: US 10,806,931 B2
(45) Date of Patent: Oct. 20, 2020

(54) DELIVERY DEVICES AND METHODS FOR LEADLESS CARDIAC DEVICES

(71) Applicant: CARDIAC PACEMAKERS, INC., St. Paul, MN (US)

(72) Inventors: Allan C. Shuros, St. Paul, MN (US); Arjun D. Sharma, St. Paul, MN (US); James V. Kauphusman, Champlin, MN (US); Brendan E. Koop, Ham Lake, MN (US); Brian Soltis, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 265 days.

(21) Appl. No.: 15/852,474

(22) Filed: Dec. 22, 2017

(65) Prior Publication Data
US 2018/0178007 A1  Jun. 28, 2018

Related U.S. Application Data

(60) Provisional application No. 62/439,267, filed on Dec. 27, 2016.

(51) Int. Cl.
*A61N 1/362* (2006.01)
*A61N 1/375* (2006.01)
(Continued)

(52) U.S. Cl.
CPC .......... *A61N 1/362* (2013.01); *A61N 1/0573* (2013.01); *A61N 1/37205* (2013.01);
(Continued)

(58) Field of Classification Search
CPC .... A61N 1/362; A61N 1/0573; A61N 1/0592; A61N 1/059; A61N 1/3756;
(Continued)

(56) References Cited

U.S. PATENT DOCUMENTS 4,301,815 A   11/1981  Doring
5,807,399 A    9/1998  Laske et al.
(Continued)

FOREIGN PATENT DOCUMENTS

EP    2818201 B1    7/2016
EP    2658599 B1   10/2016
(Continued)

*Primary Examiner* — Tuan V Nguyen
(74) *Attorney, Agent, or Firm* — Seager, Tufte & Wickhem LLP

(57) ABSTRACT

Delivery devices, systems, and methods for delivering implantable leadless pacing devices are disclosed. An example delivery device may include a tubular member and a distal holding section extending distally of a distal end of the tubular member and defining a cavity therein for receiving an implantable leadless pacing device. The delivery device may facilitate vascular delivery of the pacing device to a left side of a patient's heart. In one example, a distal tip portion may extend distal of the distal holding section and may be actuated between a closed and an opened position. When in the closed position, the distal tip portion may have a tip that can puncture or engage an opening in a septum between a left atrium and a right atrium of a patient's heart. Actuating the distal tip portion to an opened position may be utilized to dilate the puncture or opening in the septum.

20 Claims, 33 Drawing Sheets

(51) Int. Cl.
  *A61N 1/05*    (2006.01)
  *A61N 1/372*   (2006.01)
  *A61M 25/01*   (2006.01)
  *A61M 25/00*   (2006.01)
  *A61B 17/00*   (2006.01)
  *A61B 17/34*   (2006.01)

(52) U.S. Cl.
  CPC . *A61B 17/3439* (2013.01); *A61B 2017/00323* (2013.01); *A61M 25/0082* (2013.01); *A61M 25/0097* (2013.01); *A61M 25/0102* (2013.01); *A61M 25/0136* (2013.01); *A61M 25/0147* (2013.01); *A61M 2025/0004* (2013.01); *A61M 2025/0095* (2013.01); *A61M 2205/0283* (2013.01); *A61N 1/3756* (2013.01); *A61N 2001/0578* (2013.01)

(58) Field of Classification Search
  CPC . A61N 1/37512; A61F 2/3468; A61F 2/3436; A61F 2/2409; A61F 2/2418; A61F 2/243
  See application file for complete search history.

(56) References Cited

U.S. PATENT DOCUMENTS

| | | |
|---|---|---|
| 5,908,381 A | 6/1999 | Aznoian et al. |
| 6,181,973 B1 | 1/2001 | Ceron et al. |
| 6,224,725 B1 | 5/2001 | Glocker |
| 6,395,017 B1 | 5/2002 | Dwyer et al. |
| 6,409,674 B1 | 6/2002 | Brockway et al. |
| 6,497,803 B2 | 12/2002 | Glocker et al. |
| 6,551,477 B2 | 4/2003 | Glocker et al. |
| 6,582,441 B1 | 6/2003 | He et al. |
| 6,638,268 B2 | 10/2003 | Niazi |
| 6,786,918 B1 | 9/2004 | Krivoruchko et al. |
| 7,248,913 B2 | 7/2007 | Hassett |
| 7,321,798 B2 | 1/2008 | Muhlenberg et al. |
| 7,381,216 B2 | 6/2008 | Buzzard et al. |
| 7,499,758 B2 | 3/2009 | Cates et al. |
| 7,509,169 B2 | 3/2009 | Eigler et al. |
| 7,608,099 B2 | 10/2009 | Johnson et al. |
| 7,666,203 B2 | 2/2010 | Chanduszko et al. |
| 7,678,081 B2 | 3/2010 | Whiting et al. |
| 7,799,037 B1 | 9/2010 | He et al. |
| 7,840,281 B2 | 11/2010 | Kveen et al. |
| 7,937,161 B2 | 5/2011 | Hastings et al. |
| 7,993,351 B2 | 8/2011 | Worley et al. |
| 8,002,822 B2 | 8/2011 | Glocker et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,894,824 B2 | 11/2014 | Glocker et al. |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,272,155 B2 | 3/2016 | Ostroff |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,351,648 B2 | 5/2016 | Mothilal et al. |
| 9,358,387 B2 | 6/2016 | Suwito et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bornzin et al. |
| 9,468,773 B1 | 10/2016 | Anderson et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,675,798 B2 | 6/2017 | Grubac et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 2003/0078618 A1 | 4/2003 | Fey et al. |
| 2005/0101984 A1 | 5/2005 | Chanduszko et al. |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2009/0082828 A1 | 3/2009 | Ostroff |
| 2010/0274227 A1 | 10/2010 | Khairkhahan et al. |
| 2010/0292721 A1* | 11/2010 | Moberg ......... A61B 17/320758 606/159 |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0095539 A1 | 4/2012 | Khairkhahan et al. |
| 2012/0109148 A1 | 5/2012 | Bonner et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2013/0012925 A1 | 1/2013 | Berthiaume et al. |
| 2013/0035636 A1 | 2/2013 | Beasley et al. |
| 2013/0103047 A1 | 4/2013 | Steingisser et al. |
| 2013/0253342 A1 | 9/2013 | Griswold et al. |
| 2013/0253346 A1 | 9/2013 | Griswold et al. |
| 2014/0018818 A1 | 1/2014 | Somogyi et al. |

(56) References Cited

U.S. PATENT DOCUMENTS

| | | |
|---|---|---|
| 2014/0324145 A1 | 10/2014 | Eggen et al. |
| 2014/0378991 A1 | 12/2014 | Ollivier |
| 2015/0039070 A1 | 2/2015 | Kuhn et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1* | 2/2015 | Schmidt ............ A61M 25/0082 606/129 |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114157 A1 | 4/2016 | Haasl et al. |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |
| 2018/0021571 A1* | 1/2018 | Anderson ............ A61N 1/0592 606/129 |

FOREIGN PATENT DOCUMENTS

| | | |
|---|---|---|
| EP | 2651502 B1 | 11/2016 |
| EP | 2771064 B1 | 1/2017 |
| EP | 2780077 B1 | 1/2017 |

* cited by examiner

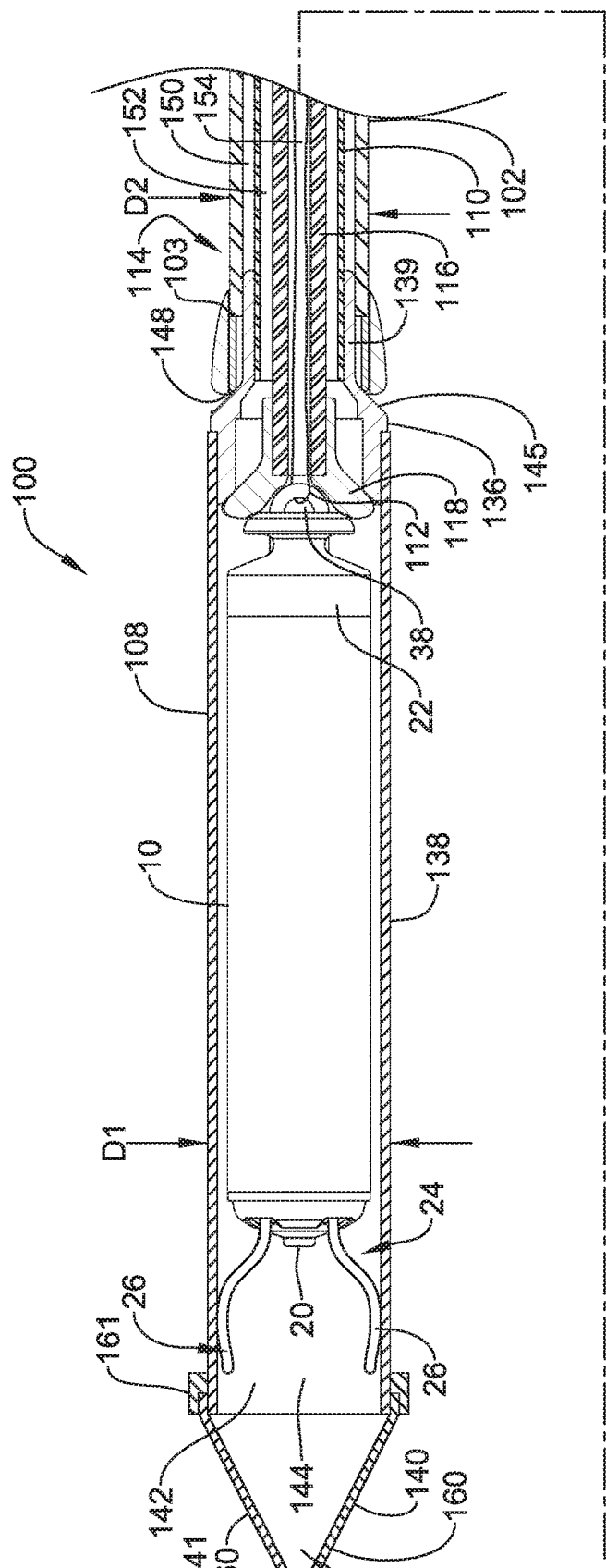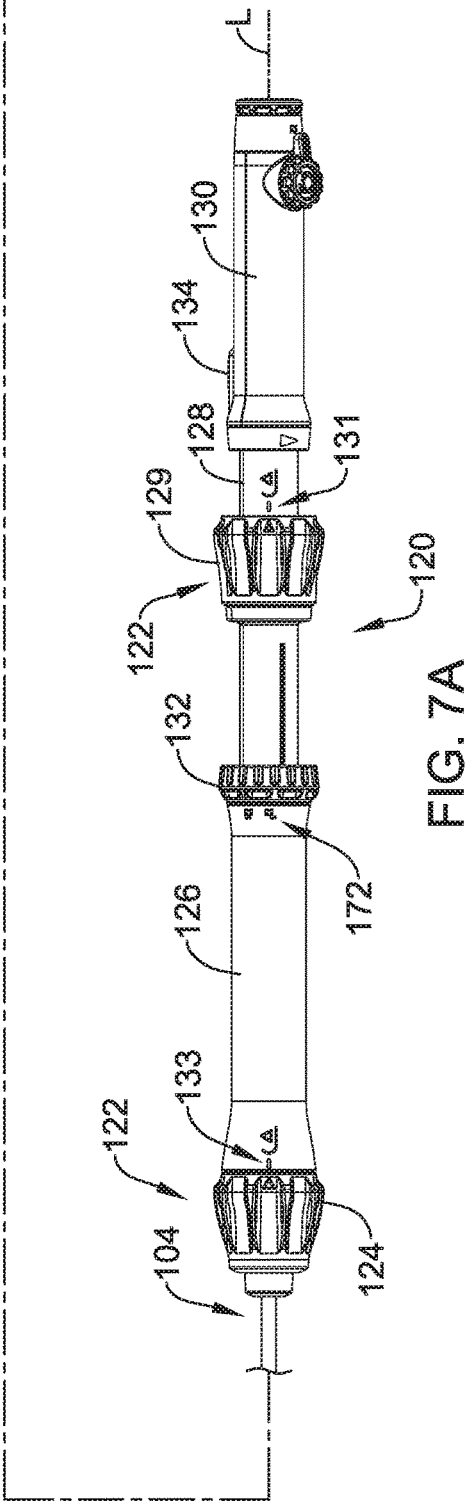
FIG. 7A

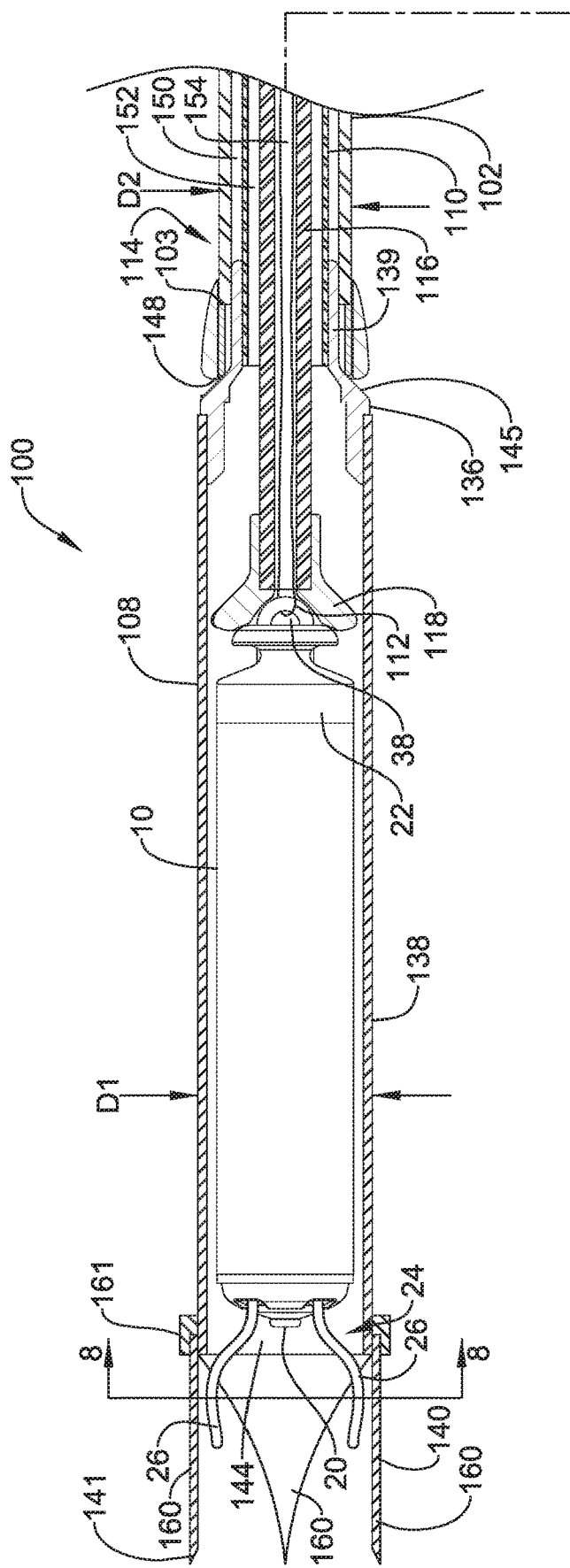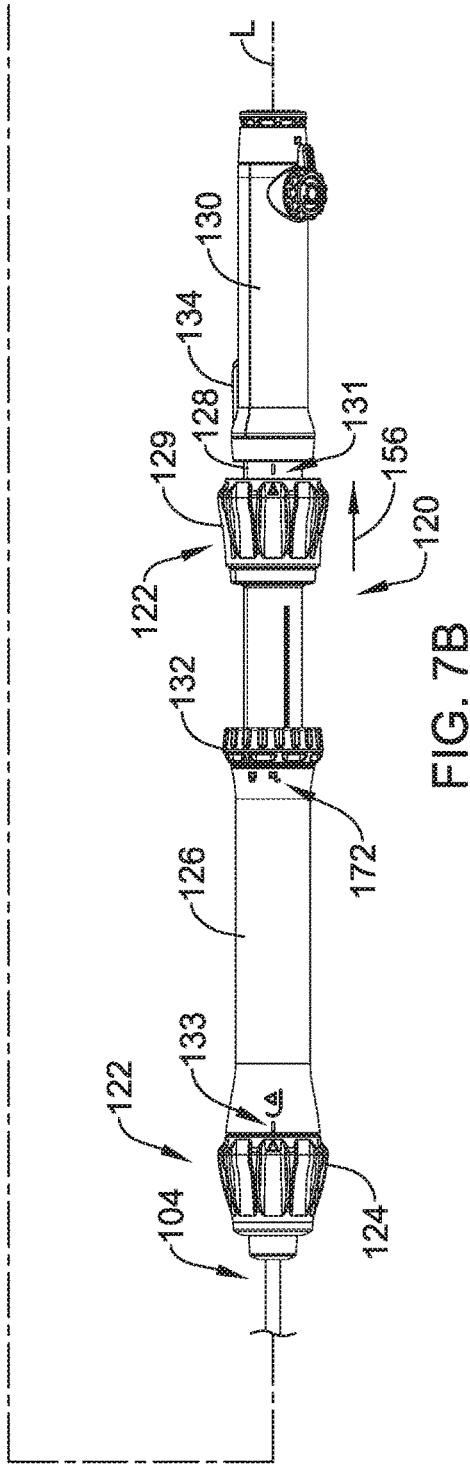
FIG. 7B

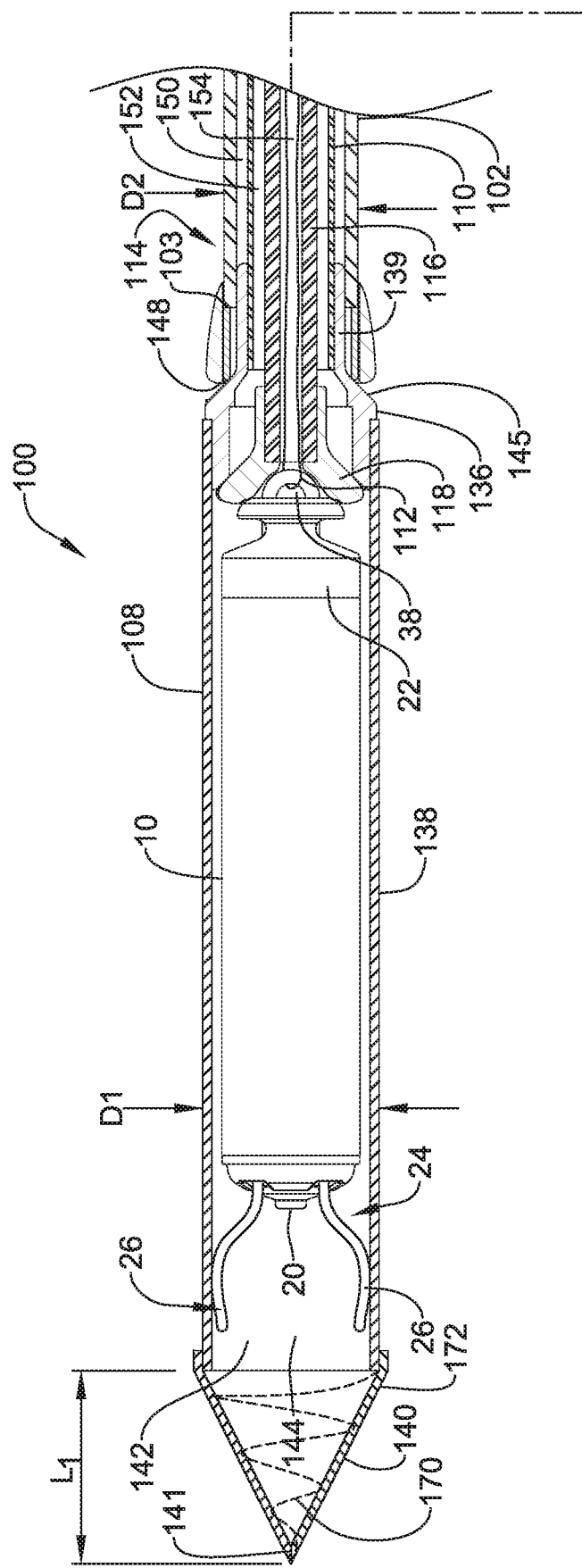
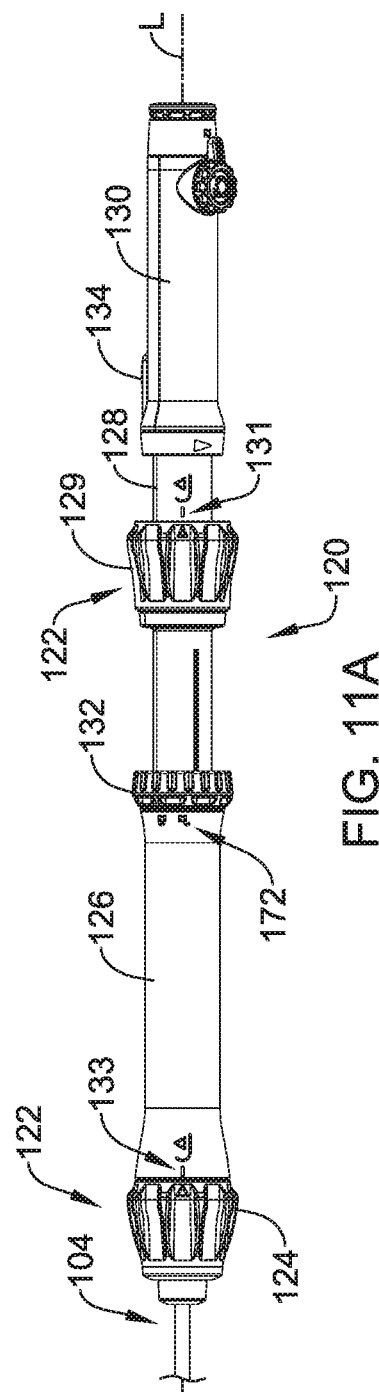
FIG. 11A

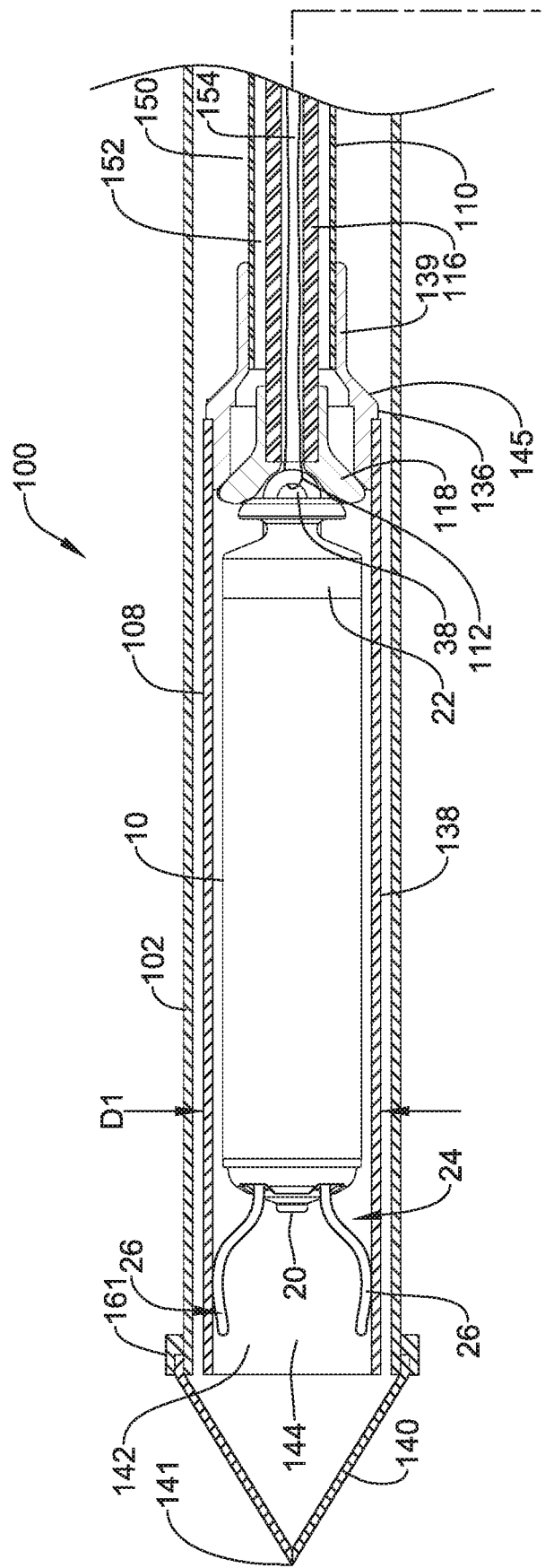

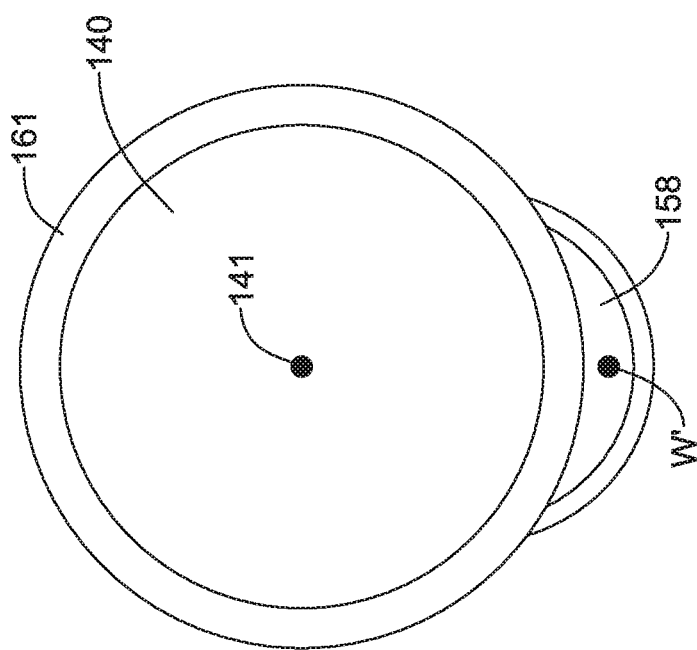

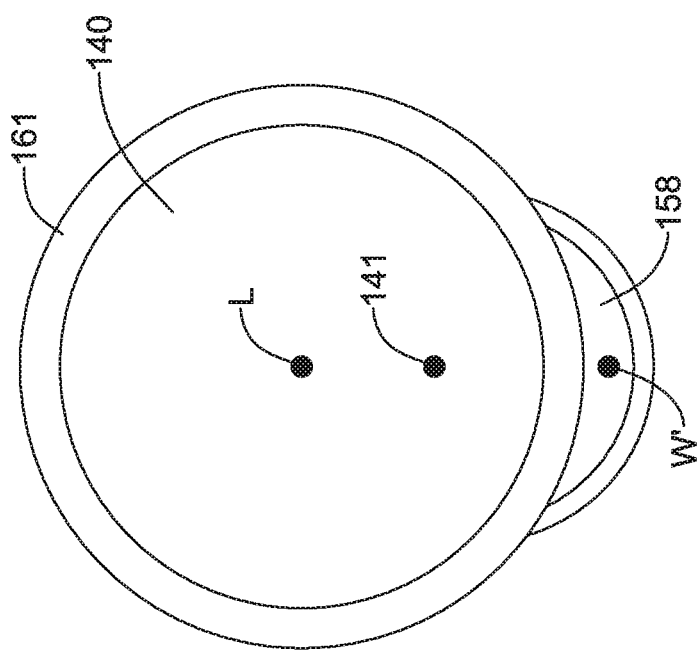

DELIVERY DEVICES AND METHODS FOR LEADLESS CARDIAC DEVICES

CROSS REFERENCE TO RELATED APPLICATIONS

The present application claims the benefit of and priority to U.S. Provisional Patent Application Ser. No. 62/439,267, filed Dec. 27, 2016, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such delivery devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a trans-septal delivery device for delivering an implantable leadless pacing device may comprise a tubular member including a lumen extending from a proximal end to a distal end thereof, a distal holding section extending distally of a distal end of the tubular member, a penetrating tip member actuatable from a closed penetrating position to an opened position, an inner member elongated from a proximal end to a distal end thereof, and a handle assembly attached to the tubular member and the inner member. The distal holding section may define a cavity therein for receiving an implantable leadless pacing device. The penetrating tip member may extend distally of a distal end of the distal holding section. The inner member may be slidably disposed within the lumen of the tubular member.

Alternatively or additionally to any of the examples above, in another example, the penetrating tip member is secured relative to a distal end region of the tubular member.

Alternatively or additionally to any of the examples above, in another example, the handle assembly may include a first hub portion affixed adjacent to the proximal end of the tubular member and a second hub portion affixed adjacent to the proximal end of the inner member, and the second hub portion may be adjustable relative to the first hub portion to adjust a longitudinal position of the inner member relative to the tubular member.

Alternatively or additionally to any of the examples above, in another example, longitudinal movement of the inner member in a first direction relative to the tubular member may actuate the tip member from the closed penetrating position to the opened position.

Alternatively or additionally to any of the examples above, in another example, longitudinal movement of the inner member in a second direction relative to the tubular member may actuate the tip member from the opened position to the closed penetrating position.

Alternatively or additionally to any of the examples above, in another example, the penetrating tip member may include electrically activated polymer and the electrically activated polymer may be activated to actuate the penetrating tip member from the closed penetrating position to an opened position.

Alternatively or additionally to any of the examples above, in another example, the trans-septal delivery device may further comprise a balloon in communication with the penetrating tip member. The balloon may be actuated to actuate the penetrating tip member from the closed penetrating position to the opened position Alternatively or additionally to any of the examples above, in another example, the tip member may comprise a plurality of plate members and each plate member may have a first end attached to the tubular member and a second free end.

Alternatively or additionally to any of the examples above, in another example, one or more of the plate members includes a longitudinally extending groove.

Alternatively or additionally to any of the examples above, in another example, the tip member may comprise an adjustable wire and a polymer material covering the adjustable wire.

Alternatively or additionally to any of the examples above, in another example, the adjustable wire may be a spiral spring.

Alternative or additionally to any of the examples above, in another example the trans-septal delivery device may further comprise a penetrating device extending distally of the penetrating tip member, and the penetrating device may have a sharp distal end configured to engage a trans-atrial septum and create an initial opening through which the penetrating tip member is inserted.

Alternatively or additionally to any of the examples above, in another example, the trans-septal delivery device may further comprise an outer tubular member including a lumen extending from a proximal end to a distal end thereof. The lumen of the outer tubular member may slidably receive the tubular member.

Alternatively or additionally to any of the examples above, in another example, the penetrating tip member may be secured relative to a distal end region of the outer tubular member.

Alternatively or additionally to any of the examples above, the distal holding section may be positionable in the lumen of the outer tubular member and advanceable distally from the outer tubular member through the penetrating tip member.

Alternatively or additionally to any of the examples above, in another example, the handle assembly may include a first actuation member actuatable from a first position to a second position to deflect the tubular member in a radial direction.

Alternatively or additionally to any of the examples above, in another example, the handle assembly may include a second actuation member actuatable from a first position to a second position to deflect the outer tubular member in a radial direction.

In another example, a trans-septal delivery device for delivering an implantable leadless pacing device may comprise an outer tubular member including a lumen extending from a proximal end to a distal end thereof, a tubular member including a lumen extending from a proximal end to a distal end thereof, a distal holding section extending distally of a distal end of the tubular member, a penetrating tip member actuatable from a closed penetrating position to an opened position, and a handle assembly. The tubular member may be slidably disposed within the lumen of the outer tubular member. The distal holding section may define a cavity therein for receiving an implantable leadless pacing device. The penetrating tip member may extend distally of a distal end of the distal holding section. The handle assembly may include a first actuation member actuatable from a first position to a second position to deflect the tubular member in a radial direction and a second actuation member actuatable from a first position to a second position to deflect the outer tubular member in a radial direction.

Alternatively or additionally to any of the examples above, in another example, the penetrating tip member may be secured relative to a distal end region of the outer tubular member.

Alternatively or additionally to any of the examples above, in another example, the penetrating tip member is secured relative to a distal end region of the tubular member.

In another example, a single stage method of delivering an implantable leadless pacing device to a target location may comprise advancing a delivery device carrying an implantable leadless pacing device to a right atrium of a patient. The delivery device may comprise a tubular member including a lumen extending from a proximal end to a distal end thereof, a distal holding section extending distally of a distal end of the tubular member, and a tip member actuatable from a closed penetrating position to an opened position. The distal holding section may define a cavity with the implantable leadless pacing device positioned therein. The tip member may extend distally of a distal end of the distal holding section. The method may further include engaging the tip member with a trans-atrial septum of the patent, actuating the tip member from the closed penetrating position to the opened position while the tip member is engaging the trans-atrial septum, and advancing the tip member, the distal holding section, and the implantable leadless pacing device through the trans-atrial septum and into a left atrium of the patient.

Alternatively or additionally to any of the examples above, in another example the method may further comprise advancing a distal end of an introducer to the right atrium of the patient, wherein the delivery device carrying the implantable leadless pacing device may be advanced to the right atrium of the patient through the introducer advanced to the right atrium.

Alternatively or additionally to any of the examples above, in another example the method may further comprise penetrating the trans-atrial septum of the patient with a penetrating device to create an initial opening in the trans-atrial septum, wherein advancing the tip member, the distal holding section, and the implantable leadless pacing device into the left atrium includes advancing the tip member into the initial opening to dilate the initial opening.

Alternatively or additionally to any of the examples above, in another example, wherein actuating the tip member from the closed penetrating position to the opened position may include advancing the implantable leadless pacing device within the cavity of the distal holding section to engage the implantable leadless pacing device with an inner surface of the tip member.

Alternatively or additionally to any of the examples above, in another example, the method may further comprise while the tip member, the distal holding section, and the implantable leadless pacing device are in the left atrium, actuating a first actuatable member in communication with an outer tubular member of the delivery device to deflect the distal holding section in a radial direction toward a left ventricle of the patient, wherein the outer tubular member has a lumen extending from a proximal end to a distal end thereof and slidably receives the tubular member in the lumen. Further, the method may include advancing the tip member, the distal holding section, and the implantable leadless pacing device into the left ventricle from the left atrium and actuating a second actuatable member in communication with the tubular member to deflect the tip member in a radial direction toward a target area on a wall of the left ventricle.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIGS. 7A and 7B are partial schematic cross-sectional side views of an example distal portion of an illustrative delivery device having an actuatable distal tip portion;

FIGS. 11A and 11B are partial schematic cross-sectional side views of an example distal portion of an illustrative delivery device having an actuatable distal tip portion;

FIGS. 15A and 15B are partial schematic cross-sectional side views of an example distal portion of an illustrative delivery device having an actuatable distal tip portion;

FIG. 16B is a distal end view of the example distal portion of the illustrative delivery device depicted in FIG. 16A;

FIG. 17B is a distal end view of the example distal portion of the illustrative delivery device depicted in FIG. 17A.

Figure 1:
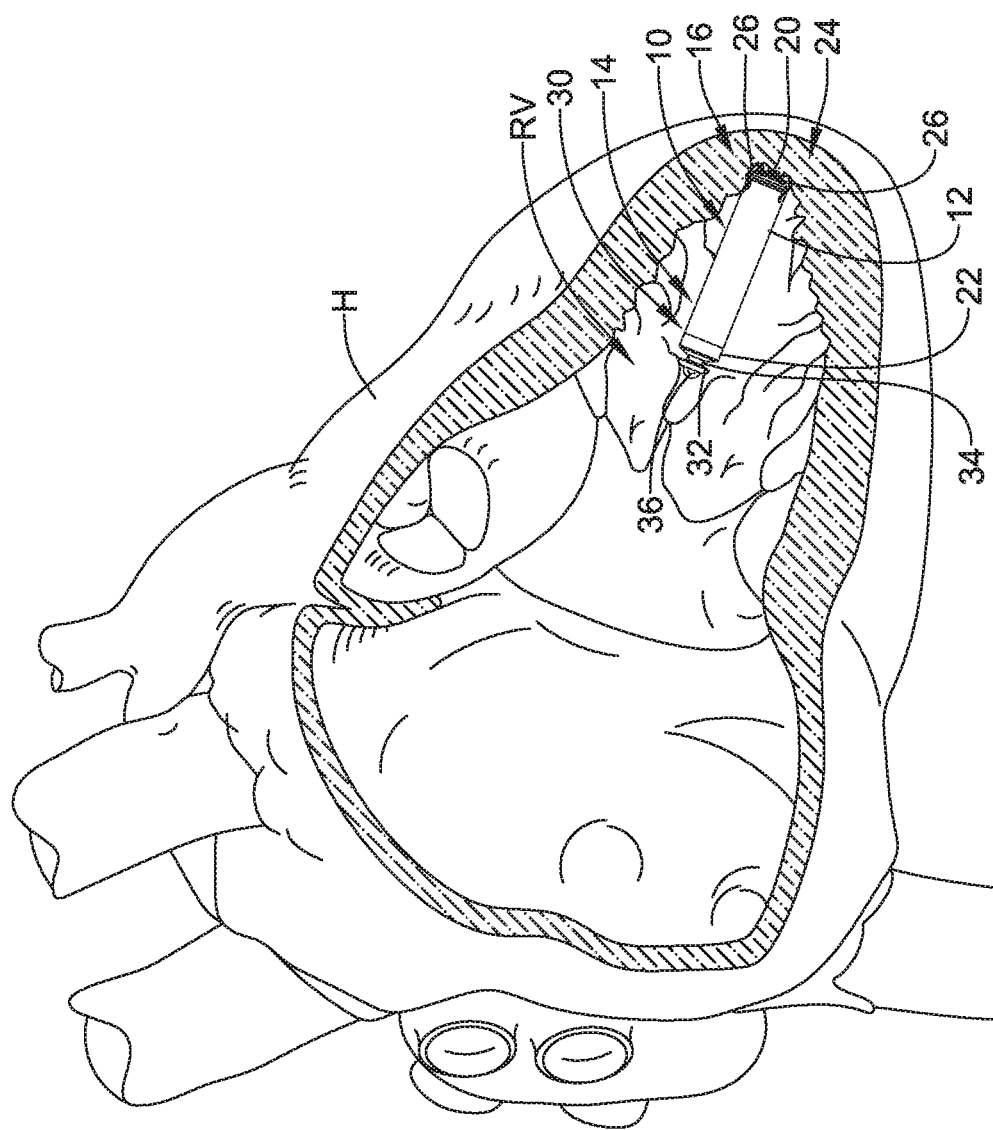
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium. From the right atrium, the capsule may be delivered through the tricuspid valve and into the right ventricle. Alternatively, or in addition, from the right atrium, the capsule may be delivered through the trans-atrial septum into the left atrium. Although the capsule may be implanted in the left atrium, the capsule may be further delivered from the left atrium, through the mitral valve and into the left ventricle. Accordingly, it may be desirable to provide delivery devices that facilitate advancement through the vasculature and through the chambers of the heart.

Figure 2:
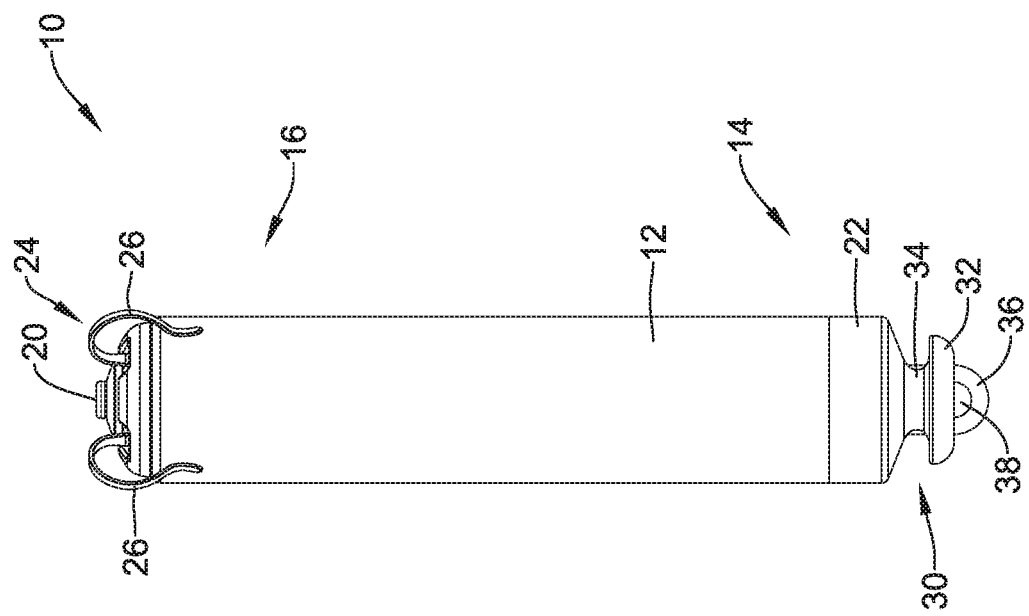
FIG. 2 is a side view of an example implantable leadless cardiac pacing device.

FIG. 1 illustrates an example implantable leadless cardiac pacing device 10 (e.g., a leadless pacemaker) implanted in a chamber of a heart H, such as the right ventricle RV. Although the implantable leadless cardiac pacing device 10 is depicted as being implanted in the right ventricle RV, the implantable leadless pacing device 10 may be implanted in any chamber of the heart H. A side view of the illustrative implantable device 10 is shown in FIG. 2.

The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks or tines 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10. The docking member 30 may further include a tether retention structure 36 extending from the head portion 32. The tether retention structure 36 may define an opening 38 configured to receive a tether or other anchoring mechanism there through. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 3:
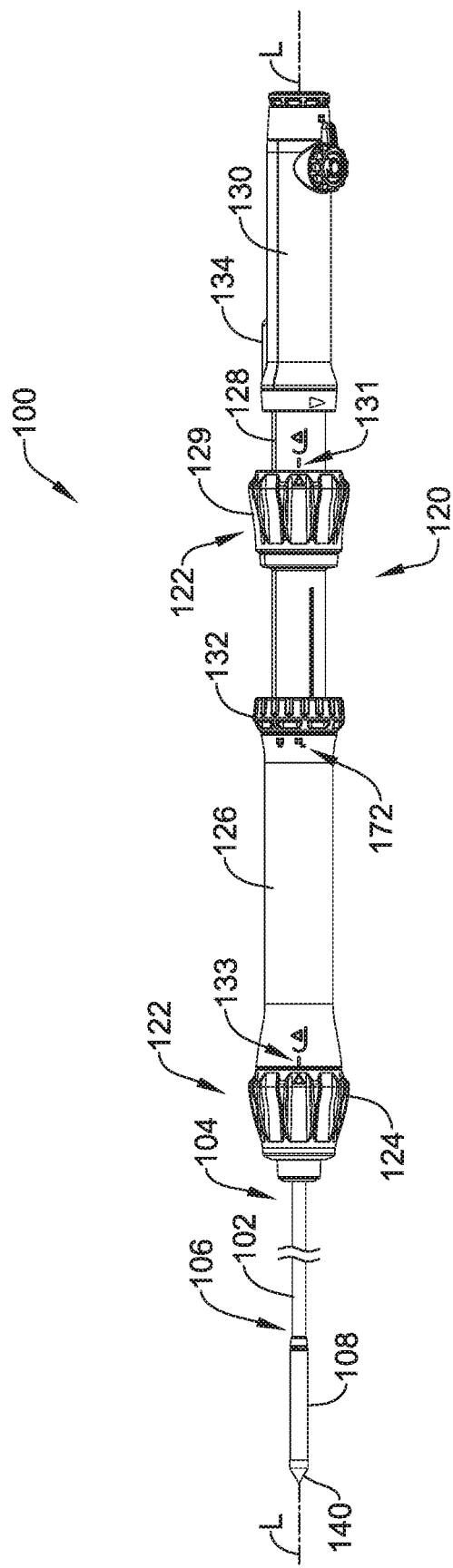
FIG. 3 is a plan view of an example delivery device for an implantable leadless cardiac pacing device.

FIG. 3 is a plan view of an illustrative delivery device 100 (e.g., a trans-septal delivery device), such as a catheter, that may be used to deliver the implantable device 10. The delivery device 100 may include an outer tubular member 102 having a proximal section 104 and a distal section 106. A tubular member 110 (e.g., an intermediate tubular member or other tubular member) may be longitudinally slidably disposed within a lumen 150 of the outer tubular member 102 (see e.g. FIG. 6). An inner member 116 may be longitudinally slidably disposed within a lumen 152 of the tubular member 110 (see e.g. FIG. 6). In some cases, the inner member 116 may have a lumen extending from a proximal end to a distal end thereof and in other cases, the inner member 116 may be or may include a portion that is an elongated solid piece of material (e.g., a wire or other elongated material). A distal holding section 108 may be attached to a distal end portion 114 of the tubular member 110. The delivery device 100 may also include a handle assembly 120 positioned adjacent to the proximal section 104 of the outer tubular member 102. In some embodiments, the outer tubular member 102 may include at least a section thereof that has an outer diameter D2 that is less than the outer diameter D1 of at least a portion of the holding section 108 (see e.g. FIG. 6).

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the tubular member 110, and a third or proximal hub portion 130 attached to, such as fixedly attached to, a proximal end section of the inner member 116. The first hub portion 126, second hub portion 128, and third hub portion 130 may be positioned in a generally telescoping arrangement and longitudinally slidable relative to each other. As will be discussed in more detail below, each of the first hub portion 126, the second hub portion 128, and the third hub portion 130 may be longitudinally slidable and rotatable relative to each other such that the outer tubular member 102, tubular member 110, and inner member 116 may be individually actuated. In some instances, it may be desirable to move the outer tubular member 102, tubular member 110, and inner member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the tubular member 110 and the inner member 116, as will be discussed in more detail below. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the tubular member 110, as will be discussed in more detail below.

Figure 4:
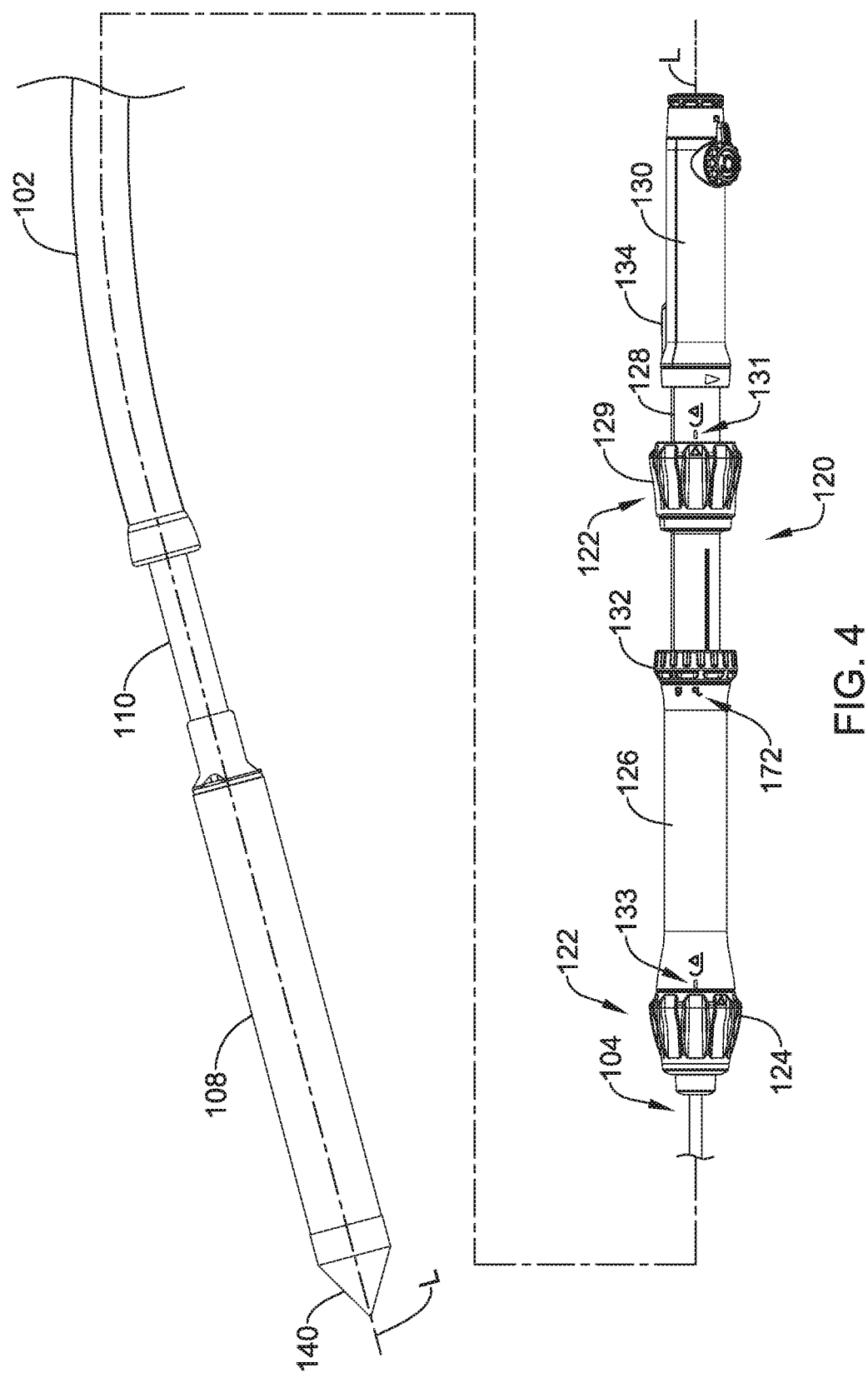
FIG. 4 is a schematic view illustrating a deflecting feature of the example delivery device of FIG. 3.
Figure 5:
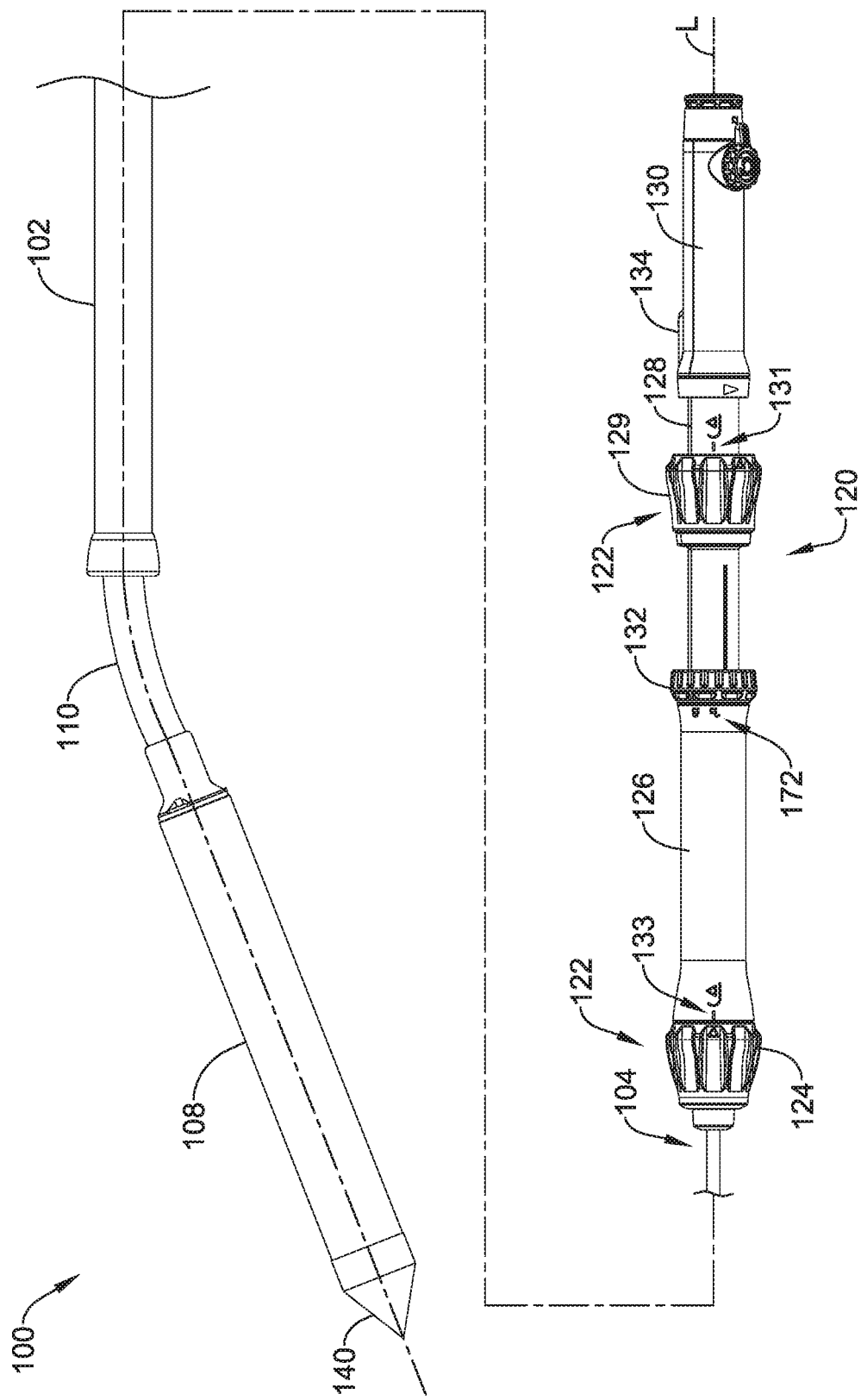
FIG. 5 is a schematic view illustrating a deflecting feature of the example delivery device of FIG. 3.

In order to more specifically place or steer the delivery device 100 to a position adjacent to the intended target, the delivery device 100 may be configured to be deflectable or articulable or steerable. Referring to FIGS. 3-5, for example, the outer tubular member 102 and/or tubular member 110 may include one or more articulation or deflection mechanism(s) that may allow for the delivery device 100, or portions thereof, to be deflected, articulated, steered and/or controlled in a desired manner. For example, the outer tubular member 102 and/or the tubular member 110 may include at least a portion thereof that can be selectively bent and/or deflected in a desired or predetermined direction (e.g., a radial direction relative to a longitudinal axis L). This may, for example, allow a user to orient the delivery device 100 such that the holding section 108 is in a desirable position or orientation for navigation or delivery of the device 10 to a target location. The outer tubular member 102 and/or the tubular member 110 may be deflected, for example, along a deflection region.

A wide variety of deflection mechanisms may be used. In some example embodiments, deflection may be effected by one or more actuation members, such as pull wire(s) extending between a distal portions of one or more of the outer tubular member 102 and the tubular member 110 and one or more actuation mechanisms 122 near the proximal ends of the outer tubular member 102 and/or the tubular member 110. In some embodiments, the outer tubular member 102 and/or the tubular member 110 may include a metal ring or tip adjacent the distal end thereof for attaching one or more pull wires thereto. When pull wires are utilized, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and/or the tubular member 110 and thereby deflect or bend the outer tubular member 102 and/or tubular member 110 in a desired manner. In addition, in some cases the one or more wires may be stiff enough so that they can also be used to provide a pushing and/or tensioning force on the outer tubular member 102 and/or the tubular member 110, for example, to "push" or "straighten" the shaft into a desired position or orientation.

In some embodiments, the actuation members may take the form of one or more continuous wires that are looped through or otherwise coupled to a distal end region of the outer tubular member 102 and/or the tubular member 110. Other embodiments are contemplated, however, including embodiments where the actuation member includes one or a plurality of individual wires that are attached, for example, to a metal or metal alloy ring adjacent the distal end region of the outer tubular member 102 and/or the tubular member 110.

The actuation mechanisms 122 may include a desired mechanism that may allow for applying tension (i.e. pulling force), or compression (i.e. pushing force), or both, on the actuation member(s). In some embodiments, the actuation mechanisms 122 may include external rotatable members 124, 129 connected to and rotatable about the longitudinal axis of the handle assembly 120. The rotatable members 124, 129 may threadingly engage an internal member that is attached to the proximal end of the actuation member(s) or pull wires.

When the external rotatable member 124 is rotated in a first rotational direction from marking 133, the internal member translates in a first longitudinal direction, thereby applying tension to the pull wire(s), which applies compression force to the shaft, so as to deflect the outer tubular member 102 from an initial position to a deflected position in a radial direction with respect to the longitudinal axis L, as shown in FIG. 4. When the external rotatable member 124 is rotated in a second rotational direction from marking 133, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

When the external rotatable member 129 is rotated in a first rotational direction from marking 131, the internal member translates in a first longitudinal direction, thereby applying tension to the pull wire(s), which applies compression force to the shaft, so as to deflect the tubular member 110 from an initial position to a deflected position in a radial direction with respect to the longitudinal axis L, as shown in FIG. 5. When the external rotatable member 129 is rotated in a second rotational direction from marking 131, the internal member translates in a second longitudinal direction, thereby reducing and/or releasing the tension on the pull wire(s), and allowing the tubular member 110 to relax back toward the initial position. Additionally, in some cases, as mentioned above, where the one or more wires may be stiff enough, rotation of the rotatable member 129 in the second rotational direction such that the internal member translates in a second longitudinal direction may apply compression to the wire(s), such that the wire(s) may apply tension to the tubular member 110 and "push" the tubular member 110 back toward an initial position, and possibly into additional positions beyond the initial position.

The one or more articulation and/or deflection mechanism(s) may also entail the outer tubular member 102 and/or the tubular member 110 including structure and/or material that may provide for the desired degree and/or location of the deflection when the compressive or tensile forces are applied. For example, the outer tubular member 102 and/or the tubular member 110 may include one or more sections that include structure and/or material configured to allow the shaft to bend and/or deflect in a certain way when a certain predetermined compressive and/or tensile force is applied. For example, the shafts may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102 and/or the tubular member 110.

In other embodiments, other articulation and/or deflection mechanism(s) are contemplated. For example, all or a portion of the delivery device 100, such as the outer tubular member 102 and/or the tubular member 110, may be made of a shape memory material, such as a shape memory polymer and/or a shape memory metal. Such materials, when stimulated by an actuation mechanism, such as a change in temperature, the application of an electrical current, or the application of a mechanical force, may change or move from a first shape to a second shape. As such, these materials and mechanisms may be used to deflect or bend the outer tubular member 102 and/or the tubular member 110 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 and/or the tubular member 110 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 and/or the tubular member 110 to be predisposed to be bent and/or deflected in a certain direction or configuration when compression and/or tension forces are applied thereto. It is contemplated that the outer tubular member 102 and/or the tubular member 110 may be a laser cut metallic tubing, a braid reinforced polymeric tubing, or other flexible tubular structure as desired.

Figure 6:
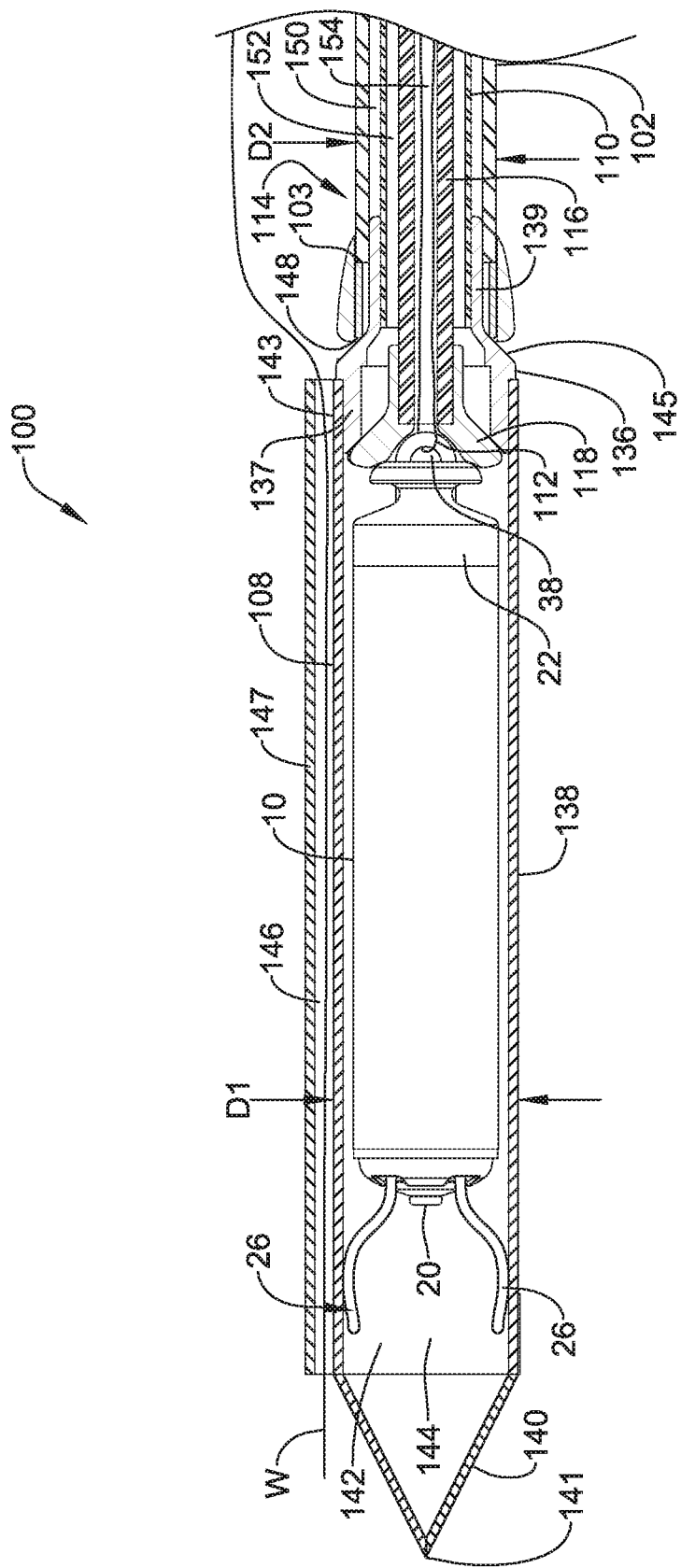
FIG. 6 is a schematic partial cross-sectional side view of an example distal portion of an illustrative delivery device having a distal tip portion.

Turning to FIG. 6, the distal holding section 108 may be configured to receive the implantable device 10 therein. For example, referring to FIG. 6, which illustrates a cross-sectional view of a distal portion of delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 and a distal tip portion 140 may extend distally from a distal end region of the body portion 138. In some cases, the distal tip portion 140 may be a penetrating tip member that is configured to penetrate through tissue of a patient's heart H, dilate a penetration opening through the heart, and/or otherwise facilitate crossing one or inner walls (e.g., walls of the trans-atrial septum or other walls) of the heart H. As discussed in greater detail below, the distal tip portion 140 may have one or more of a variety of configurations that tapers toward a distal end thereof and ends at a penetrating tip 141.

In some embodiments, all or a portion of the distal holding section 108 and/or the distal tip portion 140 may include an inner surface that may be configured to resist getting caught on the fixation mechanism 24, such as the one or more, or a plurality of hooks or tines 26 on the implantable device 10. For example, the distal holding section 108 and/or the distal tip portion 140 may include an inner layer or coating of harder or more lubricious material that resists force applied by the fixation mechanism 24 onto the inner surface of the distal holding section 108. For example, the distal holding section 108 and/or the distal tip portion 140 may include a multi-layered structure, and an inner layer may be made of a material that is harder than an outer layer.

The inner member 116 may be disposed (e.g., slidably disposed) within a lumen 152 of the tubular member 110. The inner member 116 may be engaged by a user near or at the third hub portion 130, and extend through a lumen 152 of the tubular member 110 and into the distal holding section 108. A distal portion 118 of the inner member 116 may be capable of engaging the implantable device 10, and the inner member 116 may be used to "push" the implantable device 10 out from distal holding section 108 so as to deploy and anchor the implantable device 10 within a target region (e.g., a region of the heart such as the right ventricle). The inner member 116 may have a lumen 154 extending from the proximal end 117 to a distal portion 118 thereof. Alternatively, the inner member 116 may be a wire or other elongated solid material. A tether 112 or other retaining feature may be used to releasably secure the implantable device 10 to the delivery device 100. For example, when the inner member 116 includes a lumen 154, the tether 112 may be a single or unitary length of material that may extend from a proximal end of the lumen 154, out through the distal portion 118, through the opening 38 of the implantable device 10 and return to the proximal end of the inner member 116 through the lumen 154 such that both ends of the tether 112 are positioned adjacent to the third hub portion 130. In some instances, the ends of the tether 112 may be secured within a locking feature in the third hub portion 130.

As shown in FIG. 6, the distal holding section 108 may be affixed to a distal end portion 114 of the tubular member 110. The distal holding section 108 may include a hub portion 136 and the tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

It is contemplated that the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surfaces may engage as the proximal end portion 139 is proximally retracted within the outer tubular member 102. Other coupling arrangements may be used as desired.

It is contemplated that as the outer tubular member 102 is bent to navigate the implantable device 10 to the desired location, the proximal end portion 139 may advance distally and disengage from the inner surface of the outer tubular member 102 creating a kink point or weakened region along a distal end of the tubular member 110. Proximally retracting the tubular member 110 to bring the intermediate region 145 into contact with the outer tubular member 102 at contact point 148 and/or bringing the proximal end portion 139 into the outer tubular member 102 and fixing the tubular member 110 in this configuration may help prevent migration of the distal holding section 108 during navigation of the delivery device 100 to the desired location. Such a configuration may also place the tubular member 110 in tension while the distal holding section 108 applies a compression force on the outer tubular member 102. As discussed above, a locking mechanism 132 in the handle assembly 120 may be utilized to releasably maintain the outer tubular member 102 and the tubular member 110 in a desired orientation.

In some cases, the delivery device 100 may track a wire W to facilitate delivering the implantable device 10 to a delivery location (e.g., the right atrium RA). As such, the delivery device 100 (e.g., one or more parts of the delivery device 100, such as, but not limited to, the tubular member 110 and/or the distal holding section 108) may include a lumen for receiving and tracking the wire W to the delivery location. In one example, a lumen 146 may be provided along the distal holding section 108, as shown in FIG. 6, for over-the-rail/wire tracking.

In some cases, the lumen 146 may be formed in a wall of the body portion 138 of the distal holding section 108. Alternatively, the lumen 146 may be formed in a tubular member 147 affixed to a wall of the body portion 138. If the lumen 146 is formed from the tubular member 147 affixed to a wall of the body portion 138, the tubular member 147 may be affixed to the wall of the body portion 138 by any connection technique including, but not limited to, adhesive bonding, welding, over molding, and so on. Alternatively, or in addition, to providing a lumen along the distal holding section 108, the tubular member 110 may include a lumen extending at least partially along the length thereof to receive and track a wire.

Further, other techniques are contemplated for delivering the delivery device 100 to the delivery location. For example, alternatively or in addition to tracking the wire W, the delivery device 100 may track a guide catheter (e.g., an introducer) to facilitate delivering the implantable device 10 to the delivery location (e.g., the heart H, or a portion of the heart H). In the example, a guide catheter may be inserted into the right atrium over a guide wire, the guide wire may be removed and the delivery device 100 may be inserted through the guide catheter and delivered to the delivery location. An example guide catheter, such as introducer 105, is shown in FIGS. 18A-18H.

As shown in FIG. 6, the delivery device 100 may include a tapered leading profile that is configured to facilitate the delivery device 100 crossing the trans-atrial septum (e.g., through the fossa ovalis or other portion of the trans-atrial septum). The leading profile may include the distal tip portion 140 of the delivery device 100 and/or one or more other features of the delivery device 100. The distal tip portion 140 may be secured relative to any feature of the delivery device 100 which allows the distal tip portion 140 to form a leading point when attached thereto. In one example, the distal tip portion 140 may extend from and/or may be secured to a distal end region of the distal holding section 108 (e.g., see FIGS. 6-7B, 11A, 11B, and 13A-14B) or a distal end region of the outer tubular member 102 (e.g., see FIGS. 15A and 15B).

In some cases, the leading profile of the delivery device 100 may be defined by the distal tip portion 140 and may taper toward the distal penetrating tip 141 when in a closed penetrating position. In some cases, the distal tip portion 140 may take on a general conical, pyramid, or similar distally tapering configuration when in a closed penetrating position. When in an opened position, the distal tip portion 140 may form a cylindrical or generally cylindrical leading profile that may facilitate the implantable leadless pacing device 10 being advance there through for deployment and/or recapture. Additionally or alternatively, as the distal tip portion 140 advances through the trans-atrial septum and/or transitions from the closed position to the opened position at least partially within the trans-atrial septum, the distal tip portion 140 may act to dilate an opening through the trans-atrial septum caused by the distal penetrating tip 141 or other device. As discussed in greater detail below, the distal tip portion 140 may be passively actuated (e.g., see FIGS. 7A, 7B, 11A, 11B, 15A, and 15B) and/or actively actuated (e.g., see FIGS. 13A-14B) between the closed position and the opened position. The distal tip portion 140 may be biased to one of the closed penetrating position and opened position, but this is not required.

The penetrating tip 141 may be a tip or point formed by the material of the distal tip portion 140 when the distal tip portion 140 is in a closed penetrating position. In some cases, the penetrating tip 141 may be a penetrating device and may be sharp and configured to puncture the trans-atrial septum of the heart H to create an initial opening therein. Alternatively, for example when a puncture wire (e.g., wire W with a sharp tip or other wire acting as a penetrating device) or other penetrating device is utilized to create an initial puncture into or through the trans-atrial septum, the penetrating tip 141 may be sized and configured to be inserted into an initial puncture by the puncture wire or other device. In such cases, the penetrating tip 141 may not be as sharp as is needed to puncture the trans-atrial septum The distal tip portion 140 may be formed from one or more materials. For example, the distal tip portion 140 may be formed from metallic plates, polymer plates, metal wire, elongated polymer, polymer covers, and/or one or more other materials.

FIG. 7A-10 depict one example configuration of the distal tip portion 140, where the distal tip portion 140 may be at least partially formed from a plurality of plate members 160. FIG. 7A depicts the distal tip portion 140 in a closed penetrating position and formed from a plurality of plate members 160 secured relative to a distal end of the distal holding section 108, with the second hub portion 128 of the handle assembly 120 in a first position relative to the third hub portion 130. When in the closed penetrating position, distal ends of the plurality of plate members 160 may form the penetrating tip 141.

The plate members 160 may be secured to the distal holding section 108 in any manner. In some cases, the plate members 160 may be adhesively bonded, fusion bonded, and/or over molded to secure the plate members 160 to an exterior or an interior of the distal holding section 108. Other securing techniques are contemplated. As shown in the example of FIGS. 7A and 7B, an over molding material 161 may be used to secure a proximal end of the plate members 160 to an exterior surface of the body portion 138 of the distal holding section 108. In an over molding technique, the over molding material 161 may be melted over a proximal end of the plate members 160 and the distal end of the distal holding section 108 to secure the plate members 160 to the distal holding section 108.

FIG. 7B depicts the delivery device 100 of FIG. 7A with the distal tip portion 140 actuated to an opened position as a result of the second hub portion 128 of the handle assembly 120 being adjusted in an adjusting direction 156 to a second position relative to the third hub portion 130. FIGS. 7A and 7B illustrate one example of a passive mechanism for actuating the distal tip portion 140 between a closed penetrating position and an opened position by adjusting hub portions 128 and/or 130 of the handle assembly 120 relative to one another. As shown in FIG. 7B, when the second hub portion 128 is adjusted from the first position to the second position relative to the third hub portion 130 and the implantable leadless pacing device 10 is loaded in the distal holding section 108, the inner member 116 may advance and engage the implantable leadless pacing device 10, which in turn may advance the hooks or tines 26 of the implantable leadless pacing device 10 into engagement with the distal tip portion 140 (e.g., with the plates 160) to actuate the distal tip portion 140 from the closed penetrating position to the opened position. When the implantable leadless pacing device 10 is not loaded in the distal holding section 108, the distal portion 118 of the inner member 116 may be advanced and may engage the distal tip portion 140 to actuate the distal tip portion 140 from the closed penetrating position to the opened position. Returning the second hub portion 128 to the first position or to a position in a direction of the first position relative to the third hub portion 130 may result in the distal tip portion 140 returning to the closed penetrating position from the opened position.

Figure 8:
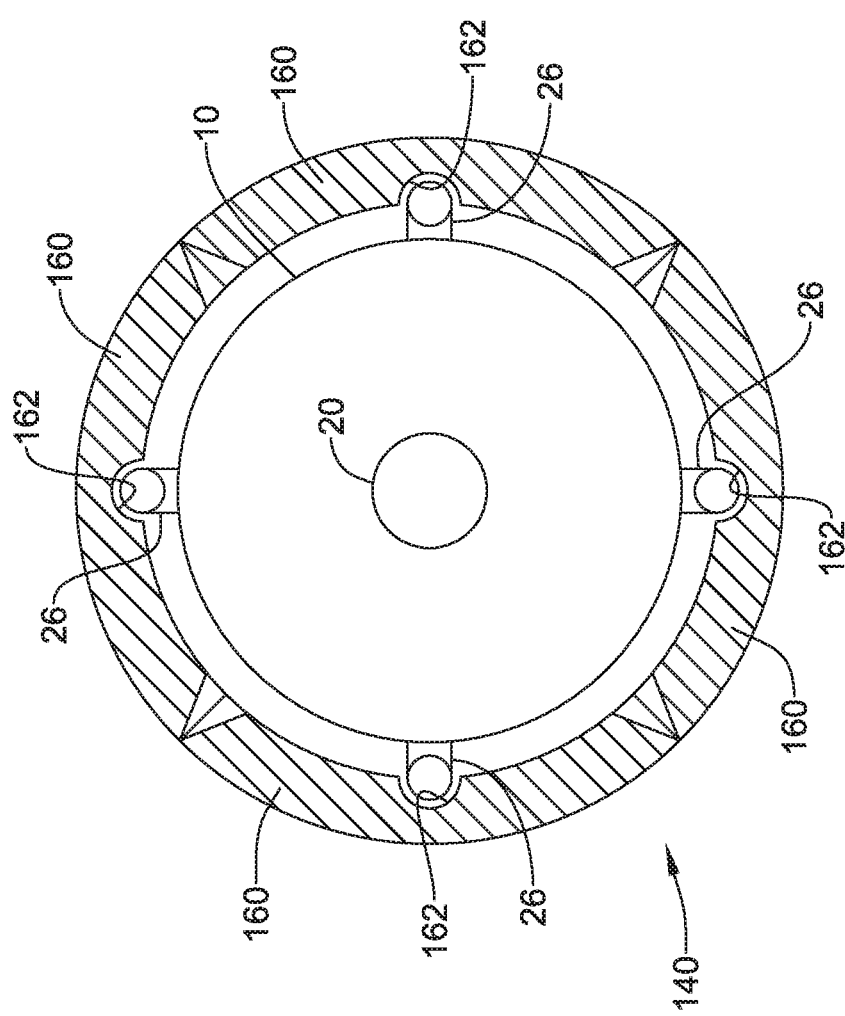
FIG. 8 is a schematic cross-sectional view of the actuatable distal tip portion of the illustrative delivery device of FIG. 7B, taken along line 8-8.

FIG. 8 is a cross-section taken along line 8-8 in FIG. 7B. As can be seen, the distal tip portion 140 may include four (4) plate members 160 each having a rounded cross-section. In one example, each plate member may have a rounded cross-sectional shape configured to form a conical shape when the distal tip portion 140 is in a closed penetrating position and configured to form a generally cylindrical shape when the distal tip portion 140 is in an opened position (e.g., as shown in FIG. 8).

The plate members 160 may be formed form any biocompatible material. In one example, the plate members 160 may be formed from a shape memory metal. The shape memory metal of the plate members 160 may be configured to change from a first shape forming the conical shaped closed penetrating position of distal tip portion 140 with the other plate member 160 to a generally cylindrical shaped opened position of the distal tip portion in response to actuation of the distal tip portion 140. In one example, the shape memory metal may include a nickel-titanium alloy, such as nitinol. However, this is not required and one or more other shape memory materials or other material may be utilized for the plate members 160.

Although four plate members 160 are depicted, the distal tip portion 140 formed from plate members 160 may have any number of plate members 160. For example, the distal tip portion 140 may be formed from one (1) plate member 160, two (2) plate members 160, three (3) plate members 160, four (4) plate members 160, five (5) plate members 160, or other number of plate members 160.

In some cases, the plate members 160 may include a longitudinally extending groove 162. The grooves 162 may have any cross-sectional shape configured to receive a tine or hook 26 of the implantable leadless pacing device 10 as the implantable leadless pacing device 10 advances into and/or through the distal tip portion 140. As shown in FIG. 8, the groves 162 may have a rounded cross-sectional shape, but this is not required and each groove 162 may have the same or different cross-sectional shape as one or more other groove 162.

Figure 9:
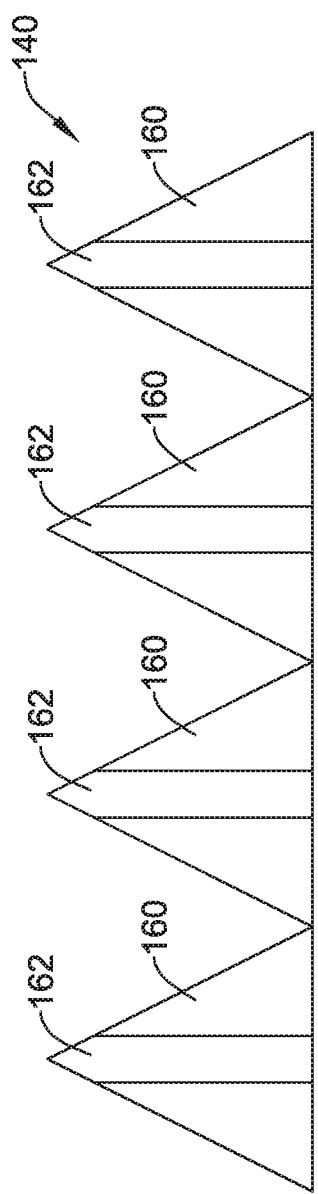
FIG. 9 is a schematic plan view of an interior side of segments from the actuatable distal tip portion of the illustrative delivery device of FIGS. 7A and 7B.

FIG. 9 depicts the four plate members 160 forming the distal tip portion 140 of FIGS. 7A-8, but in a spread out configuration. As can be seen, each plate member 160 may have a general triangular shape defined by a perimeter with a groove 162 extending longitudinally from a proximal end to a distal end of the plate members 160. Although the plate members 160 are depicted as being flat, each plate member 160 may have a rounded cross-section, as discussed above with reference to FIG. 8. Alternative shapes for each plate member 160 are contemplated and a shape of the plate members 160 should not be limited to the triangular shape depicted in FIG. 9.

Figure 10:
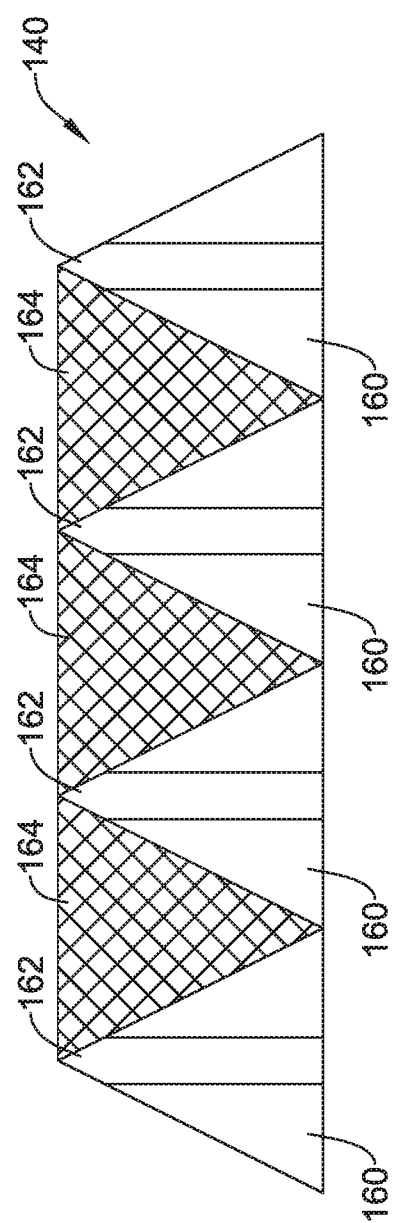
FIG. 10 is a schematic plan view of an interior side of segments from an example actuatable distal tip portion of an illustrative delivery device.

FIG. 10 depicts four plate members 160 forming the distal tip portion 140 in a same configuration as shown in FIG. 9, but with a filler material 164 extending at least partially between the plate members 160. In one example, the filler material 164 may fill the space between the plate members 160 when the distal tip portion 140 is in an opened position and may be received within (e.g., folded into) the distal tip portion 140 when the distal tip portion 140 is in the closed penetrating position. Further, in some cases, the filler material 164 may facilitate transitioning between the closed penetrating position and the opened position of the distal tip portion 140.

The filler material 164 may be any type of material. For example, the filler material 164 may be a polymer, a fabric, or other material that may be flexible and configurable to fill spaces between the plate members 160 when the distal tip portion 140 is in the opened position and to allow the plate members 160 to close when the distal tip portion 140 is in the closed penetrating position. In some cases, the filler material 164 may be a flexible webbing.

FIGS. 11A-12B depict one example configuration of the distal tip portion 140, where the distal tip portion 140 may be formed from one or more wires 170 and a flexible material 172. FIG. 11A depicts the distal tip portion 140 in a closed penetrating position and formed from a wire 170 and flexible material 172 secured relative to a distal end of the distal holding section 108, with the second hub portion 128 of the handle assembly 120 in a first position relative to the third hub portion 130. When in the closed penetrating position, the wire 170 may have a spiral form and a distal end of the wire 170 and the flexible material 172 may form the penetrating tip 141. Further, when in the closed penetrating position, the distal tip portion 140 may have a longitudinal length L1.

The wire(s) 170 and the flexible material 172 may take on any configuration with respect to one another. For example, the wire(s) 170 may be secured to an exterior surface of the flexible material 172, the wire(s) 170 may be secured to an interior surface of the flexible material 172, or the wire(s) 170 may be encased within the flexible material 172. Further, the wire(s) 170 may be secured to the flexible material 172 through any connection technique including, but not limited to, adhesive boding, over molding, insert molding, welding, and/or through one more other connection techniques.

Figure 11B:
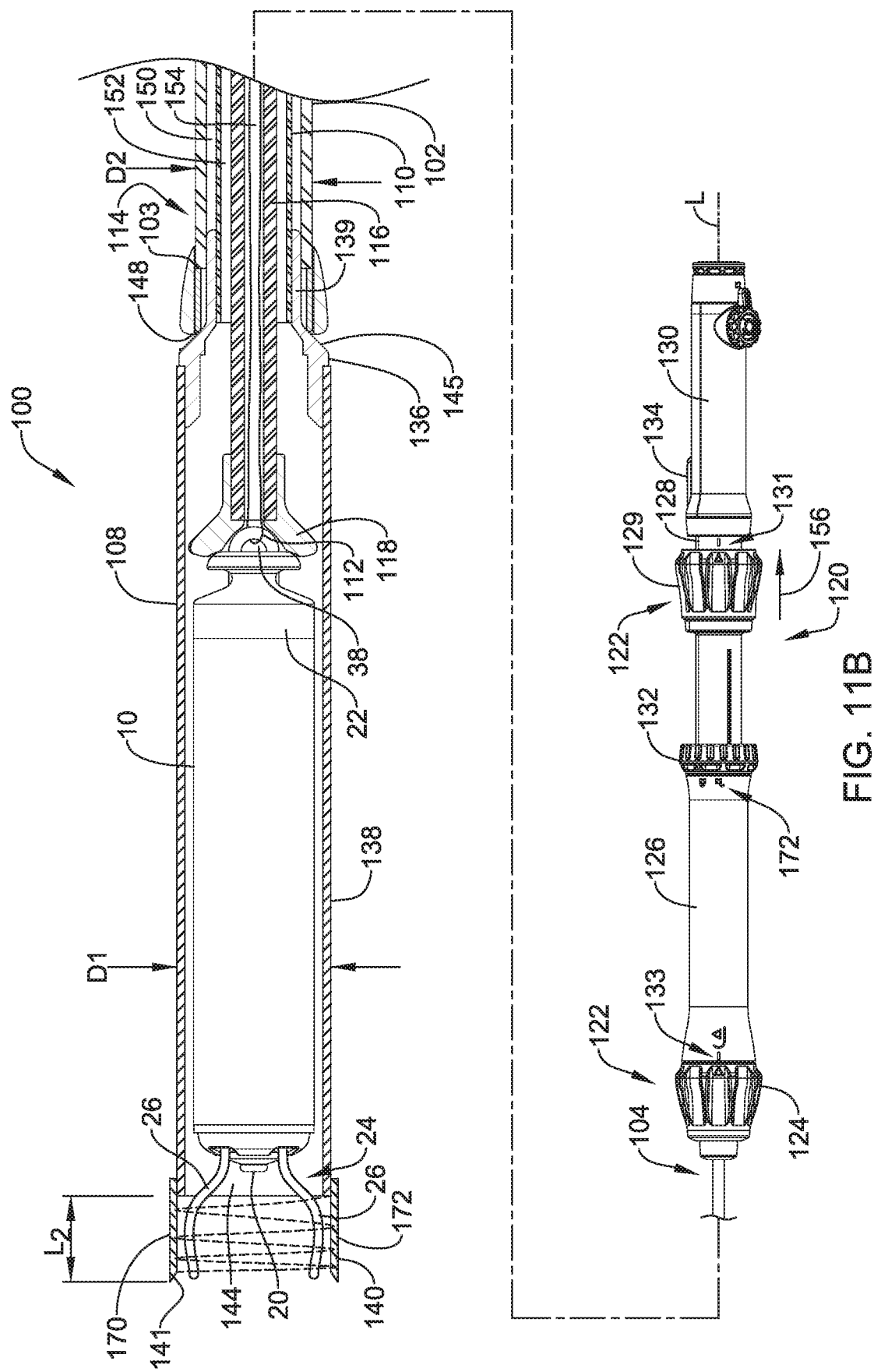

The wire 170 and/or the flexible material 172 may be secured to the distal holding section 108 in any manner. In some cases, one or more of the wire 170 and the flexible material 172 may be adhesively bonded, fusion bonded, insert bonded, and/or over molded to the distal holding section 108 to secure the distal tip portion 140 to an exterior or an interior of the distal holding section 108. Other securing techniques are contemplated. As shown in the example of FIGS. 11A and 11B, an adhesive bonding technique may be used to secure a proximal end of the flexible material 172 to an exterior surface of the body portion 138 of the distal holding section 108. In such cases, the wire 170 may be attached to and/or encased in the flexible material and an adhesive may be applied to an interior surface and/or an exterior surface of the body portion 138 to facilitate adhesively bonding the distal tip portion 140 to the distal holding section 108. In alternative connection techniques, only the wire 170 or the wire 170 and the flexible material 172 may be directly bonded or otherwise attached to the distal holding section 108.

FIG. 11B depicts the delivery device 100 of FIG. 11A with the distal tip portion 140 actuated to an opened position as a result of the second hub portion 128 of the handle assembly 120 being adjusted in an adjusting direction 156 to a second position relative to the third hub portion 130. FIGS. 11A and 11B illustrate one example of a passive mechanism for actuating the distal tip portion 140 between a closed penetrating position and an opened position by adjusting hub portions 128 and/or 130 of the handle assembly 120 relative to one another. As shown in FIG. 11B, when the second hub portion 128 is adjusted from the first position to the second position relative to the third hub portion 130 and the implantable leadless pacing device 10 is loaded in the distal holding section 108, the inner member 116 may advance and engage the implantable leadless pacing device 10, which in turn may advance the hooks or tines 26 of the implantable leadless pacing device 10 into engagement with the distal tip portion 140 (e.g., with the wire 170 and/or the flexible material 172) to actuate the distal tip portion 140 from the closed penetrating position to the opened position. When the implantable leadless pacing device 10 is not loaded in the distal holding section 108, the distal portion 118 of the inner member 116 may be advanced and may engage the distal tip portion 140 to actuate the distal tip portion 140 from the closed penetrating position to the opened position. Returning the second hub portion 128 to the first position or to a position in a direction of the first position relative to the third hub portion 130 may result in the distal tip portion 140 returning to the closed penetrating position from the opened position.

As shown in FIG. 11B, once the tines or hooks 26 (or distal portion 118, not shown) engage the distal tip portion 140, the wire 170 retracts its spiral configuration, and with the flexible material 172 forms a general cylindrical cross-sectional shape in the distal tip portion 140. Once the wire 170 and the flexible material 172 have expanded, the distal tip portion 140 in the opened position may have a longitudinal length L2, where a length L2 may be shorter than a length L1.

Figure 12A:
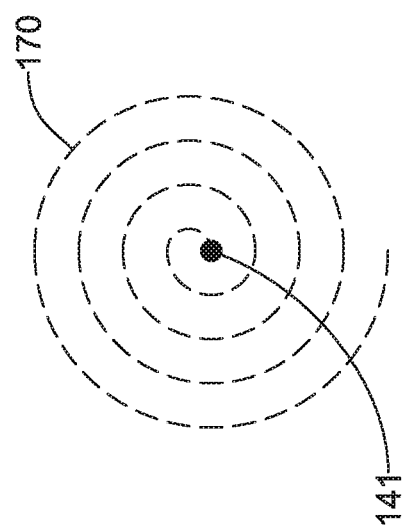
FIGS. 12A and 12B are schematic plan views from a distal end of a wire of the actuatable distal tip portion of the illustrative delivery device depicted in FIGS. 11A and 11B, respectively.
Figure 12B:
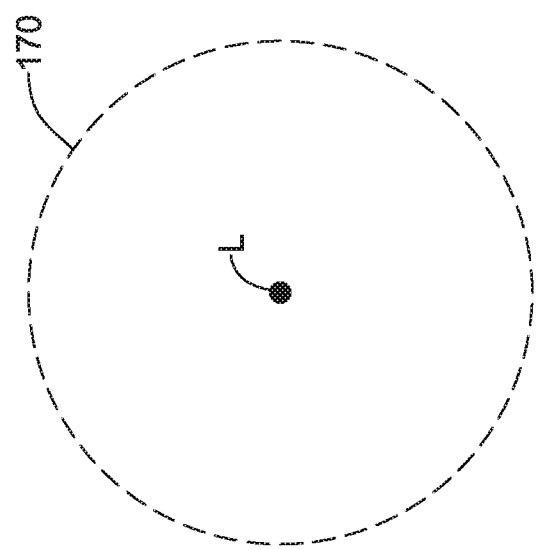

FIGS. 12A and 12B depict plan views of the wire 170 from a distal end thereof when the distal tip portion 140 is in a closed penetrating position, as shown in FIG. 11A, and when the distal tip portion 140 is in an opened position, as shown in FIG. 11B, respectively. As can be seen in FIG. 12A, the wire 170 may take on a spiral form when the distal tip portion 140 is in a closed penetrating position, such that the distal end of the wire 170 may form the penetrating tip 141. As can be seen from FIG. 12B, the wire 170 may unravel its spiral shape seen in FIG. 12A such that its windings may be concentric or substantially concentric about the longitudinal axis L when the distal tip portion 140 is in the opened position.

FIGS. 13A-14B depict generic distal tip portions 140 and active actuation mechanisms for actuating the distal tip portion 140 between the closed penetrating position and the opened position. Active mechanisms for actuating the distal tip portion 140 between the closed penetrating position and the opened position may include, but are not limited to, balloon mechanisms with a hydraulic or pneumatic pump, electrically activated polymer mechanisms, and/or other active mechanisms. As generic distal tip portions 140 are depicted in FIGS. 13A-14B, it should be understood that the active actuation mechanisms disclosed herein may be utilized with any configuration of the distal tip portion 140.

Figure 13A:
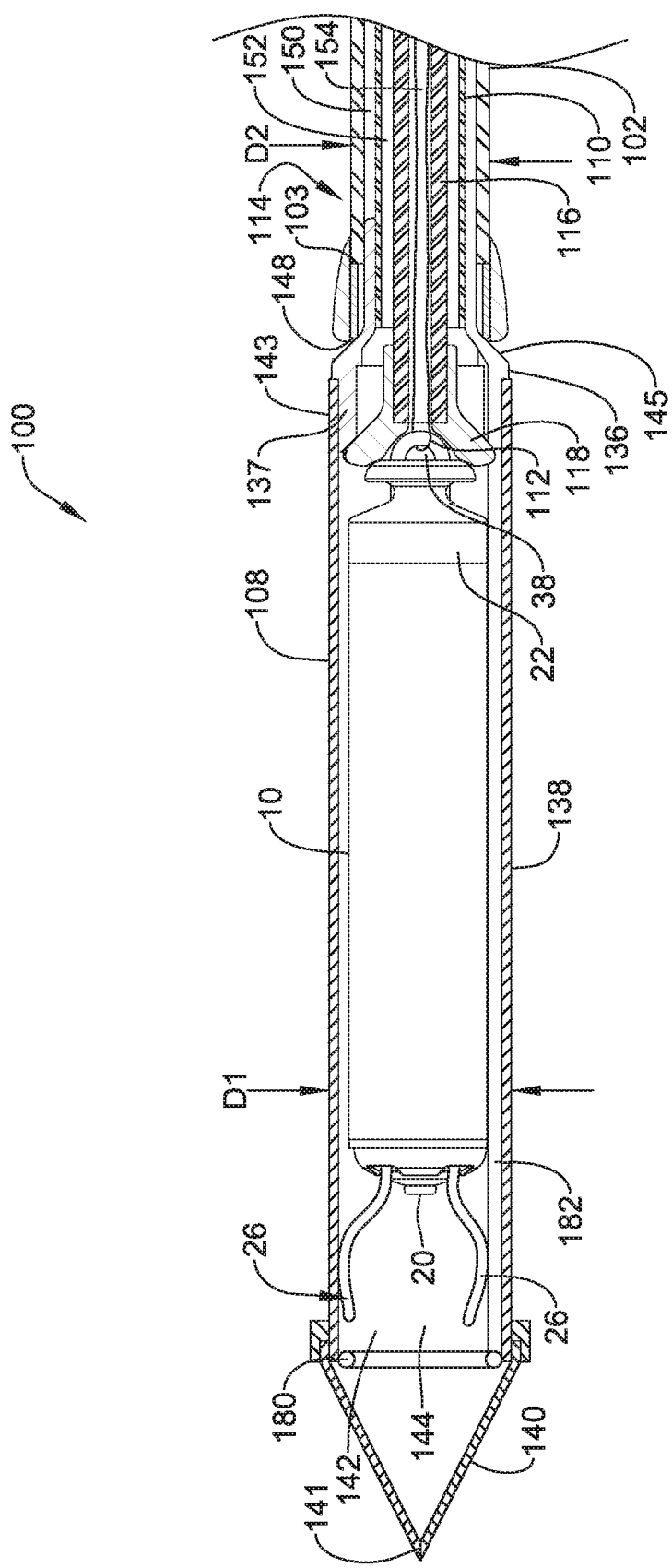
FIGS. 13A and 13B are partial schematic cross-sectional side views of an example distal portion of an illustrative delivery device having an actively actuated actuatable distal tip portion.
Figure 13B:
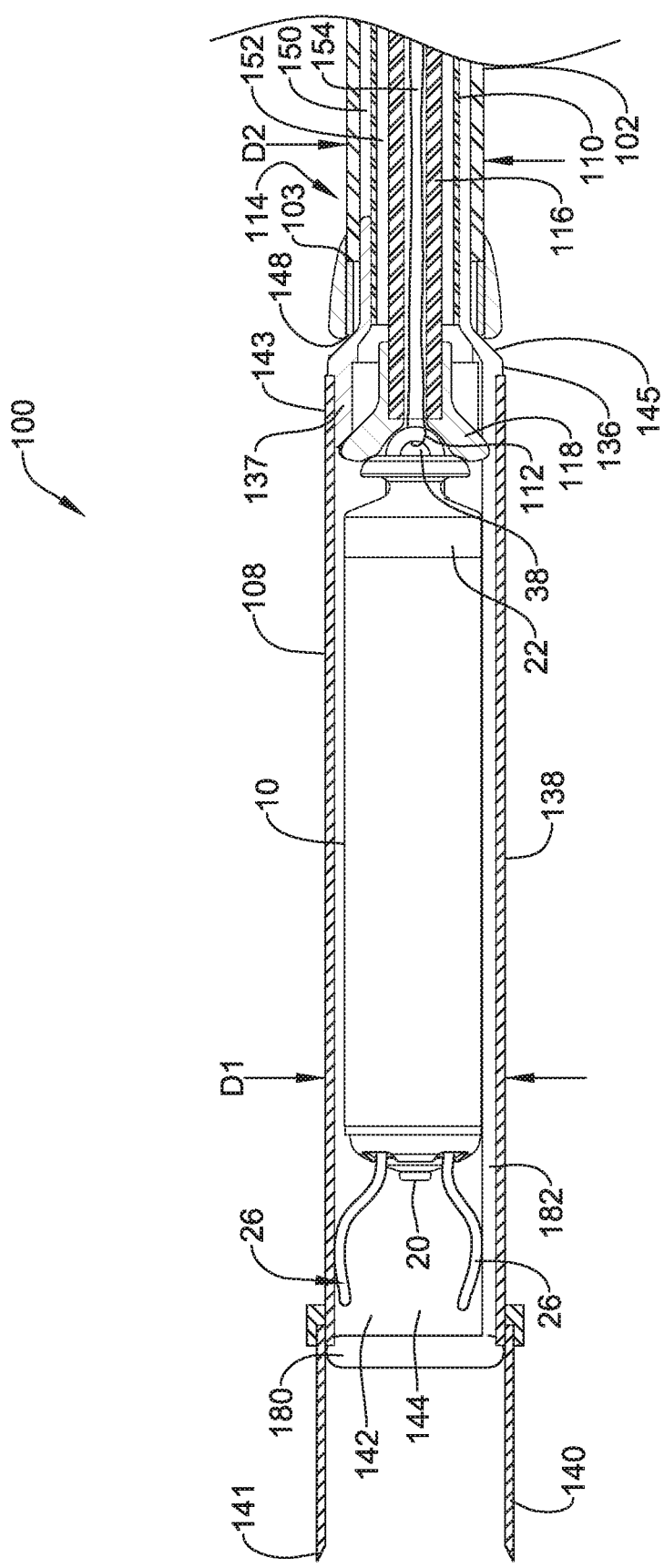

Turning to FIGS. 13A and 13B, a balloon actuation mechanism for actively actuating the distal tip portion between the closed penetrating position and the opened position is shown. In the example, a balloon 180 may be located at a distal end of the body portion 138 of the distal holding section 108. Although the balloon 180 is shown in FIGS. 13A and 13B as being located at an interior of the distal holding section 108, the balloon 180 may be located at or adjacent an exterior of the distal holding section 108 and/or at any location about the distal holding section 108 at which the balloon 180 may engage the distal tip portion 140 when in an expanded configuration.

In some cases, the distal tip portion 140 may be biased to the closed penetrating position and when the balloon 180 is in a deflated state, as shown in FIG. 13A, the distal tip portion 140 may be in the closed penetrating position. In other cases, the distal tip portion 140 may be biased to the opened position and when the balloon 180 is in the deflated state, the distal tip portion 140 may be in the opened position.

The balloon 180 may be in communication with an inflation lumen 182. The inflation lumen 182 may extend to a proximal end of the tubular member 110 and/or to the handle assembly 120. Fluid may be passed through the inflation lumen 182 to the balloon 180. When the balloon 180 receives fluid, the balloon 180 may expand to actuate the distal tip portion 140 between the closed penetrating position and the opened position. Further, fluid may be withdrawn through the inflation lumen 182 (or a different lumen, not shown) to deflate the balloon 180 to actively actuate the distal tip portion 140 from the opened position to the closed penetrating position. Fluid may be provided to the balloon 180 through the inflation lumen 182 via a hydraulic pump, a pneumatic pump, and/or other pump.

FIG. 13B depicts the balloon 180 after it has received fluid from the inflation lumen 182 and is in an expanded configuration. When expanded, the balloon 180 may engage a proximal end region of the distal tip portion 140 and cause the distal tip portion 140 to actuate from the closed penetrating position to the opened position. Removal of the fluid from the balloon 180 may result in the distal tip portion 140 returning to the closed penetrating position, as shown in FIG. 13A.

Figure 14A:
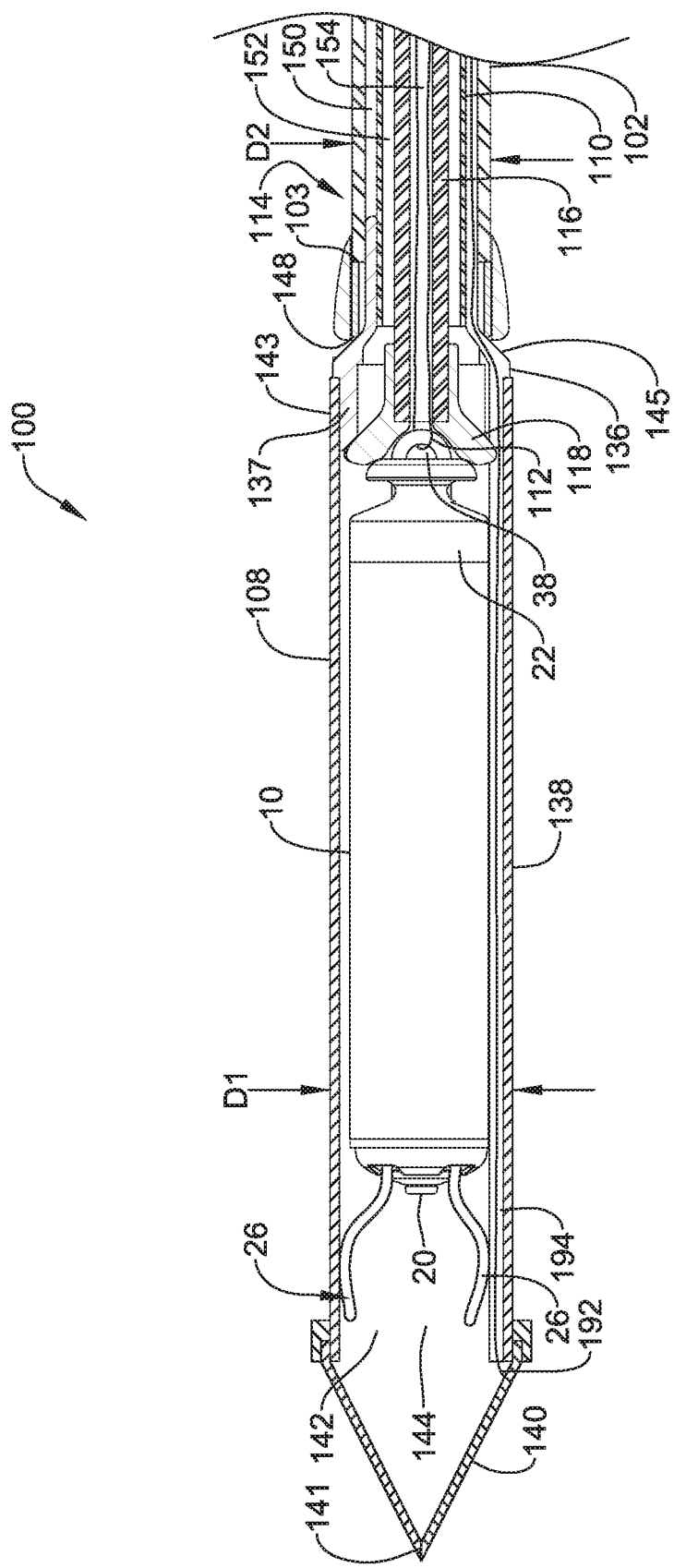
FIGS. 14A and 14B are partial schematic cross-sectional side views of an example distal portion of an illustrative delivery device having an actively actuated actuatable distal tip portion.
Figure 14B:
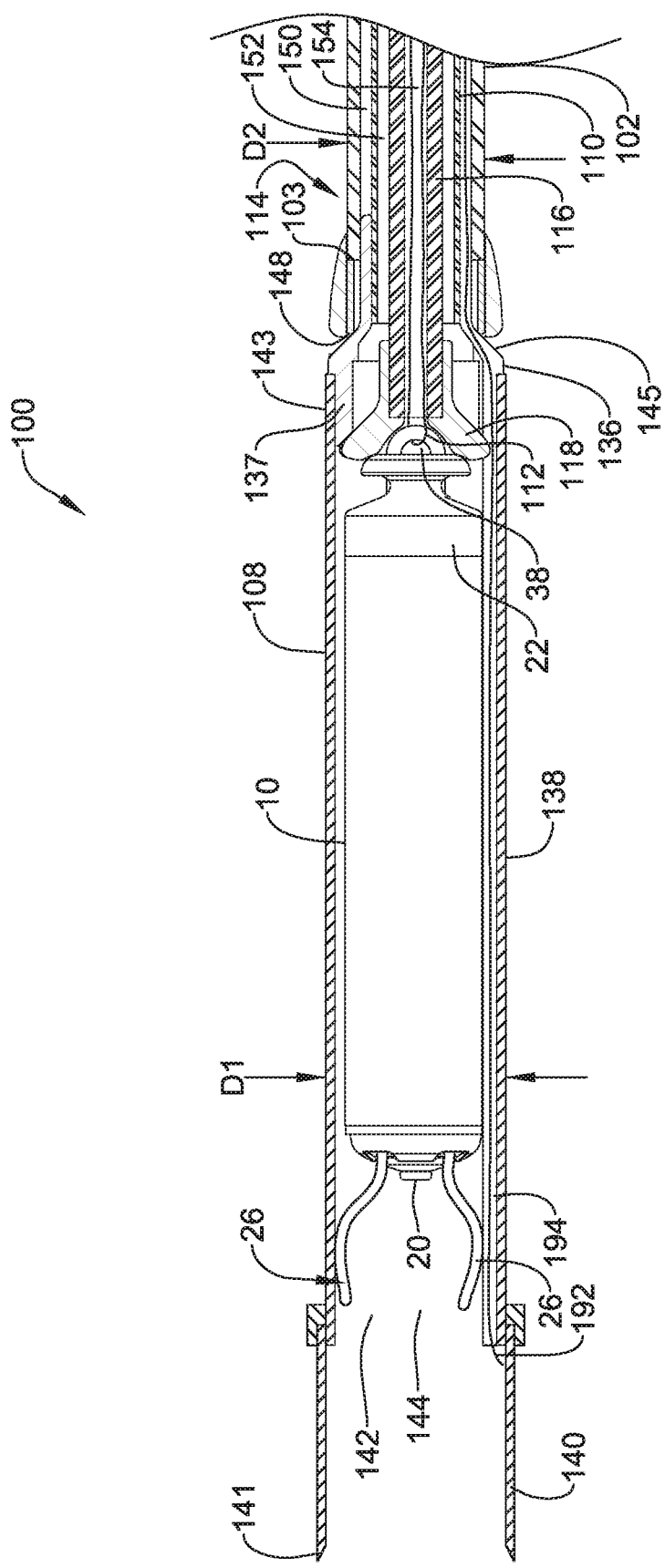

Turning to FIGS. 14A and 14B, an active mechanism for actuating the distal tip portion between the closed penetrating position and the opened position that utilizes an electrically activated polymer 190 is shown. Electrically activated polymers are polymers that may exhibit a change in size or shape when stimulated by electricity. In the example, an electrically activated polymer 190 may form at least part of the material of the distal tip portion 140. In one example, with reference to the distal tip portions 140 utilizing plate members 160, the electrically activated polymer 190 may be utilized as or as part of filler material 164 between adjacent plate members 160 and/or as or as part of the material of the plate members 160. In another example, with reference to the distal tip portions 140 utilizing wire(s) 170 and flexible material 172, the electrically activated polymer may be used as or part of one or more of the wire(s) 170 and the flexible material 172. It is contemplated that the electrically activated polymer 190 may be utilized in one or more other manners to actuate the distal tip portion between the closed penetrating position and the opened position.

In some cases, the distal tip portion 140 may be biased to the closed penetrating position and when a current or electric field is not applied to the electrically activated polymer, as shown in FIG. 14A, the distal tip portion 140 may be in the closed penetrating position. In other cases, the distal tip portion 140 may be biased to the opened position and when a current or electric field is not applied to the electrically activated polymer, the distal tip portion 140 may be in the opened position.

The electrically activated polymer 190 may be in communication with an electrode 192. The electrode 192 may extend to a proximal end of the tubular member 110 and/or to the handle assembly 120. Current or an electrical field may be passed through the electrode 192 to the electrically activated polymer 190. When the electrically activated polymer 190 receives the current or electrical field, the electrically activated polymer 190 may change shapes from an inactive shape to an active shape to actuate the distal tip portion 140 between the closed penetrating position and the opened position. Further, current or the electrical field may be turned off or removed from the electrode 192 and/or the electrically activated polymer 190 such that the electrically activated polymer 190 returns to its inactive shape to actuate the distal tip portion 140 from the opened position to the closed penetrating position. In some cases, the electrode 192 may extend within an electrode lumen 194 proximally from the electrically activated polymer 190, but this is not required.

FIG. 14B depicts the distal tip portion 140 after the electrically activated polymer 190 has received current or an electrical field from the electrode 192 and electrically activated polymer is in the active shape. When in the active shape, the electrically activated polymer 190 may either form the opened distal tip portion 140 or cause other material of the distal tip portion 140 to actuate from the closed penetrating position to the opened position. Removal of the current or electrical field from the electrically activated polymer 190 may result in the distal tip portion 140 returning to the closed penetrating position, as shown in FIG. 14A.

Figure 15B:
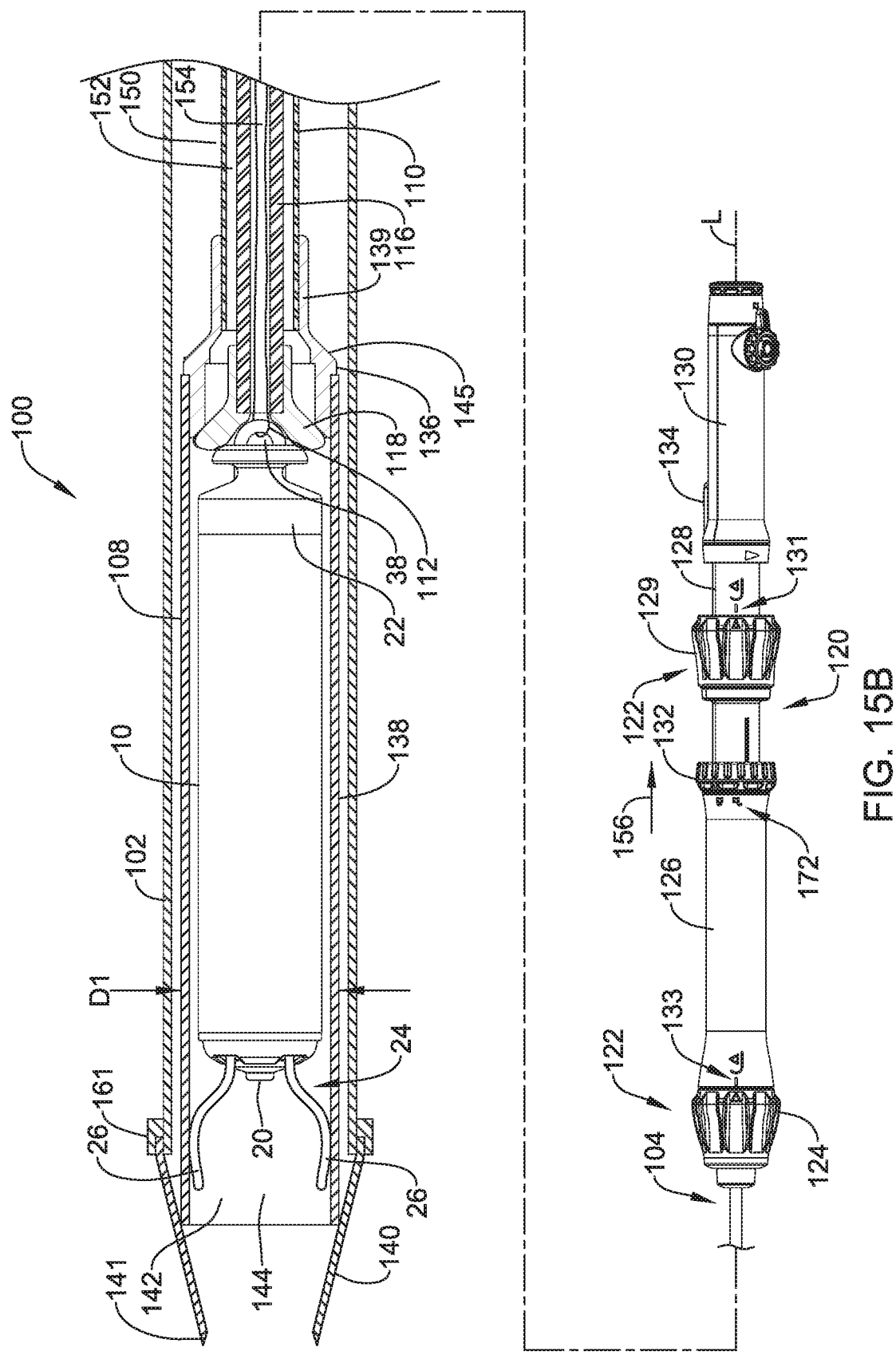

FIGS. 15A and 15B depict a generic distal tip portion 140 having a penetrating tip 141, where the distal tip portion 140 may be secured relative the outer tubular member 102. As shown in FIGS. 15A and 15B, the outer tubular member 102 may have an inner diameter configured to extend over the distal holding section 108 extending from the tubular member 110.

FIG. 15A depicts the distal tip portion 140 extending distally of the distal holding section 108 and in the closed penetrating position. When in the closed penetrating position, distal end of the distal tip portion 140 may form the penetrating tip 141.

The distal tip portion 140 may be secured to the outer tubular member 102 in any manner. In some cases, the distal tip portion 140 may be adhesively bonded, fusion bonded, insert molded, and/or over molded to an exterior or an interior of the outer tubular member 102 to secure the distal tip portion 140 relative to a distal end region of the outer tubular member 102. Other securing techniques are contemplated. As shown in the example of FIGS. 15A and 15B, the over molding material 161 may be used to secure a proximal end of the distal tip portion 140 to an exterior surface of the outer tubular member 102. In an over molding technique, the over molding material 161 may be melted over a proximal end of the distal tip portion 140 and the distal end region of the outer tubular member 102 to secure the distal tip portion 140 to the outer tubular member 102.

FIG. 15B depicts the delivery device 100 of FIG. 15A with the distal tip portion 140 actuated to an opened position as a result of the first hub portion 126 of the handle assembly 120 being adjusted in an adjusting direction 156 to a second position relative to the second hub portion 128. FIGS. 15A and 15B illustrate one example of a passive mechanism for actuating the distal tip portion 140 between a closed penetrating position and an opened position by adjusting hub portions 128 and/or 130 of the handle assembly 120 relative to one another. Alternatively or in addition, one or more other passive mechanism or active mechanism for actuating the distal tip portion 140 between the closed penetrating position and the opened position may be utilized.

As shown in FIG. 15B, when the first hub portion 126 is adjusted from the first position to the second position relative to the second hub portion 128, a distal end of the tubular member 110 may advance into engagement with the distal tip portion 140 to actuate the distal tip portion 140 from the closed penetrating position to the opened position. Returning the first hub portion 126 to the first position or to a position in a direction of the first position relative to the second hub portion 128 may result in the distal tip portion 140 returning to the closed penetrating position from the opened position. In addition to or as an alternative to engaging the distal end of the distal holding section 108 with the distal tip portion 140, one or more of the tines or hooks 26 of the implantable leadless pacing device 10 or the distal end 118 of the inner member 116 may engage the distal tip portion 140 to actuate the distal tip portion 140 between the closed penetrating position and the opened position.

As discussed above, the delivery device 100 may track a wire to facilitate delivering the implantable device 10 to a delivery location (e.g., the right atrium RA or other portion of the heart H). As such, the delivery device 100 (e.g., one or more parts of the delivery device 100, such as, but not limited to, the outer tubular member 102) may include a lumen for receiving and tracking a wire W' to the delivery location. In one example, a lumen 158 may be provided along an outer portion of the outer tubular member 102, as shown in FIGS. 16A-17B, and/or along an inner portion of the outer tubular member 102 (not shown) for wire tracking.

Figure 16A:
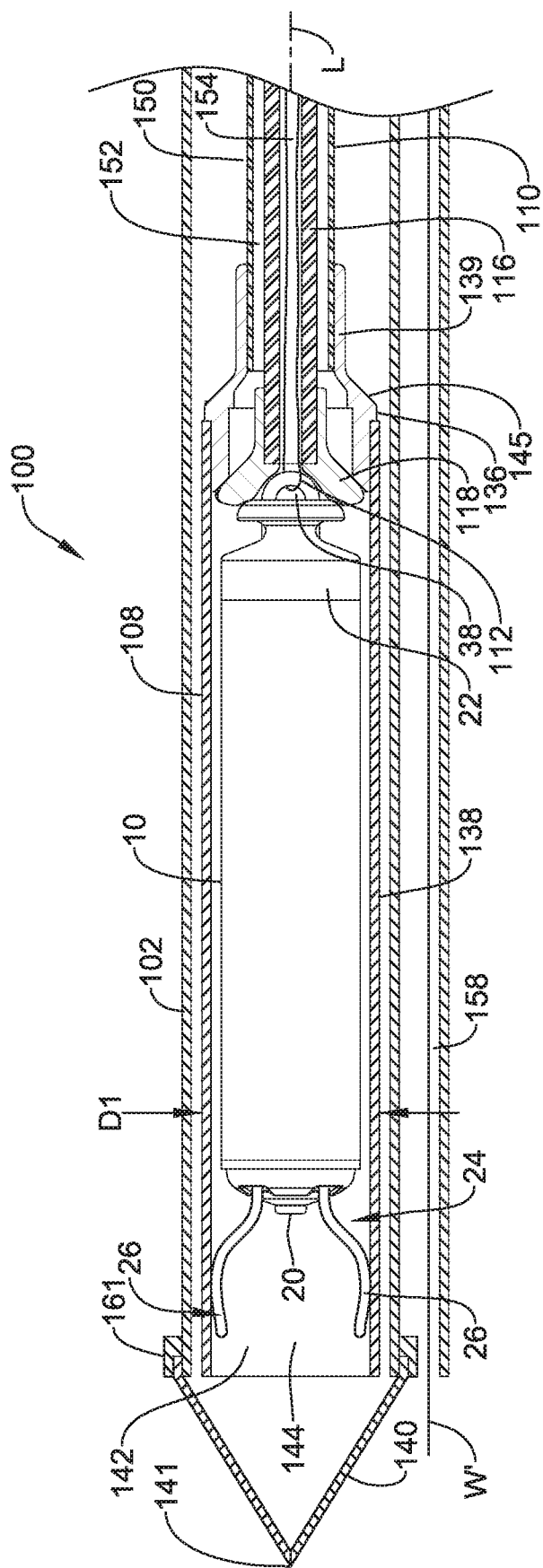
FIG. 16A is a partial schematic cross-sectional side view of an example distal portion of an illustrative delivery device having an actuatable distal tip portion.
Figure 17A:
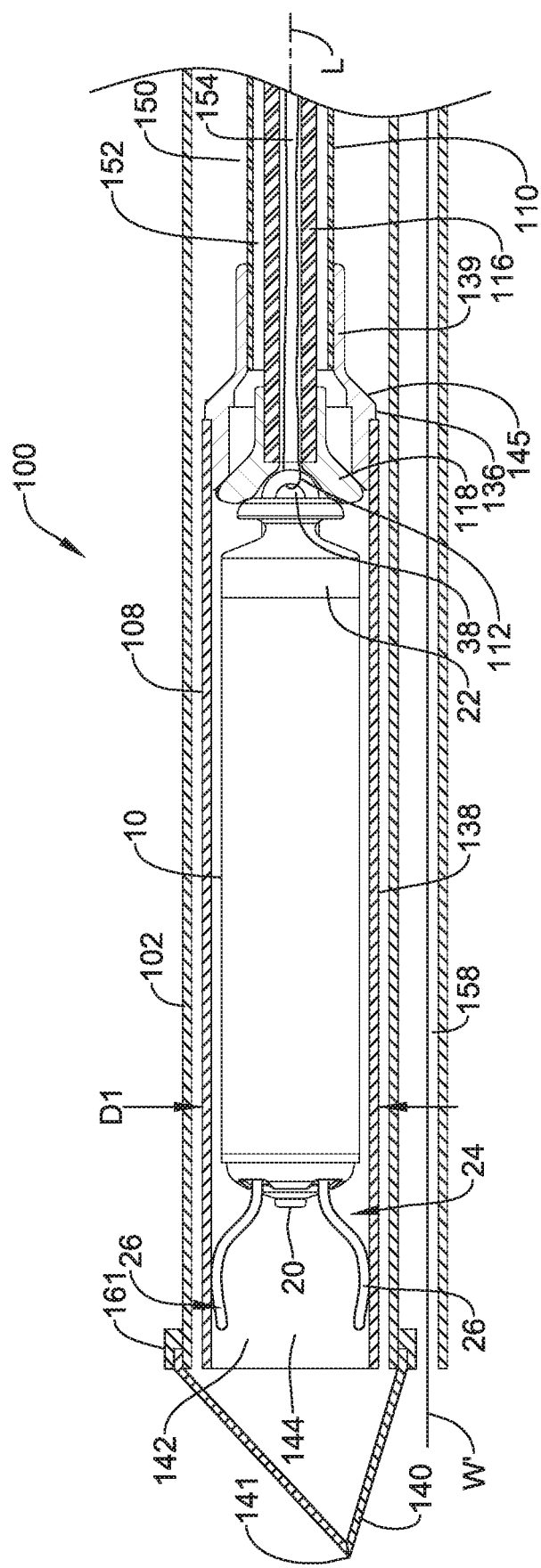
FIG. 17A is partial schematic cross-sectional side view of an example distal portion of an illustrative delivery device having an actuatable distal tip portion.

In some cases, the lumen 158 may be formed in a wall of the outer tubular member 102, as shown in FIGS. 16A and 17A. Alternatively, the lumen 158 may be formed in a lumen tubular member affixed to a wall of the outer tubular member 102. If the lumen 158 is formed from the lumen tubular member affixed to a wall of the outer tubular member 102, the lumen tubular member may be affixed to the wall of the outer tubular member by any connection technique including, but not limited to, adhesive bonding, welding, over molding, and so on.

FIG. 16A and FIG. 16B depict a delivery device 100 having a lumen 158 for tracking over wire W' and/or for receiving a puncture wire (e.g., wire W' or other penetrating wire) or other penetrating device and a penetrating tip 141 that is aligned or substantially aligned with the longitudinal axis L of the delivery device 100. The wire W' or other penetrating device may have a sharp distal tip and may be configured from metal, a polymer, or a composite of metal and polymer. In use, once the wire W' or other device punctures the trans-atrial septum, the penetrating tip 141 may engage a puncture location and the distal tip portion 140 may be advanced there through.

FIG. 17A and FIG. 17B depict a delivery device 100 having a lumen 158 for tracking over wire W' and/or for receiving a puncture wire (e.g., wire W' or other penetrating wire) or other penetrating device and a penetrating tip that is offset with respect to the longitudinal axis L of the delivery device 100. In use, once the wire W' or other device punctures the trans-atrial septum, the penetrating tip 141 may engage a puncture location and the distal tip portion 14 may be advanced there through. In cases where the penetrating tip 141 may be offset from the longitudinal axis L toward a side of the delivery device including lumen 158, the offset nature of the penetrating tip 141 near the lumen 158 may facilitate engaging the penetrating tip 141 with a puncture opening in the trans-atrial septum caused by the wire W' or other penetrating device.

Although FIGS. 16A-17B depict a lumen 158 on an outer portion of the outer tubular member 102, the lumen may be disposed on an inner portion of the outer tubular member 102 such that a received wire W' or penetrating device passes through the distal tip portion 140 prior to extending distally of the penetrating tip 141. In such cases, the distal tip portion 140 may be actuated to an open position once the distal tip portion 140 is positioned within the right atrium to allow the received wire W' or penetrating device to exit an interior of the delivery device 100.

Further, in instances when a guide catheter or introducer (e.g., introducer 105, as shown in FIGS. 18A-18H) is utilized to deliver the delivery device 100 to the right atrium RA or other portion of the heart H, the delivery device 100 may not utilize a lumen 146 or a lumen 158 as the delivery device may track the guide catheter or introducer already inserted into the right atrium RA, but this is not required. Further, a penetrating device (e.g., wire W, wire W', or other penetrating device) may be advanced within the guide catheter or introducer to the right atrium and may puncture the trans-atrial septum before or while the delivery device 100 is located in the right atrium RA.

FIGS. 18A-18H depict steps in an example single stage method of delivering an implantable leadless pacing device to a target location. In the example method, a target location may be located in the left ventricle LV of a patient's heart H, but the method may be utilized to arrive at other target locations.

The delivery device 100 may be utilized in the method to cross the trans-atrial septum and deliver the implantable leadless pacing device 10 into the target location. However, one or more other devices may be utilized instead of or in addition to the delivery device 100. For example, in some cases a wire or needle may be utilized to provide an initial puncture of a patient's fossa ovalis in the trans-atrial septum and then the delivery device 100 may be utilized to dilate the initial puncture and cross the trans-atrial septum. Further, although the delivery device 100 of FIGS. 15A and 15B is shown in FIGS. 18A-18H being used in the single stage method of delivering an implantable leadless pacing device to a target location, other delivery devices 100 including, but not limited to, the delivery devices 100 described herein may be utilized.

Figure 18A:
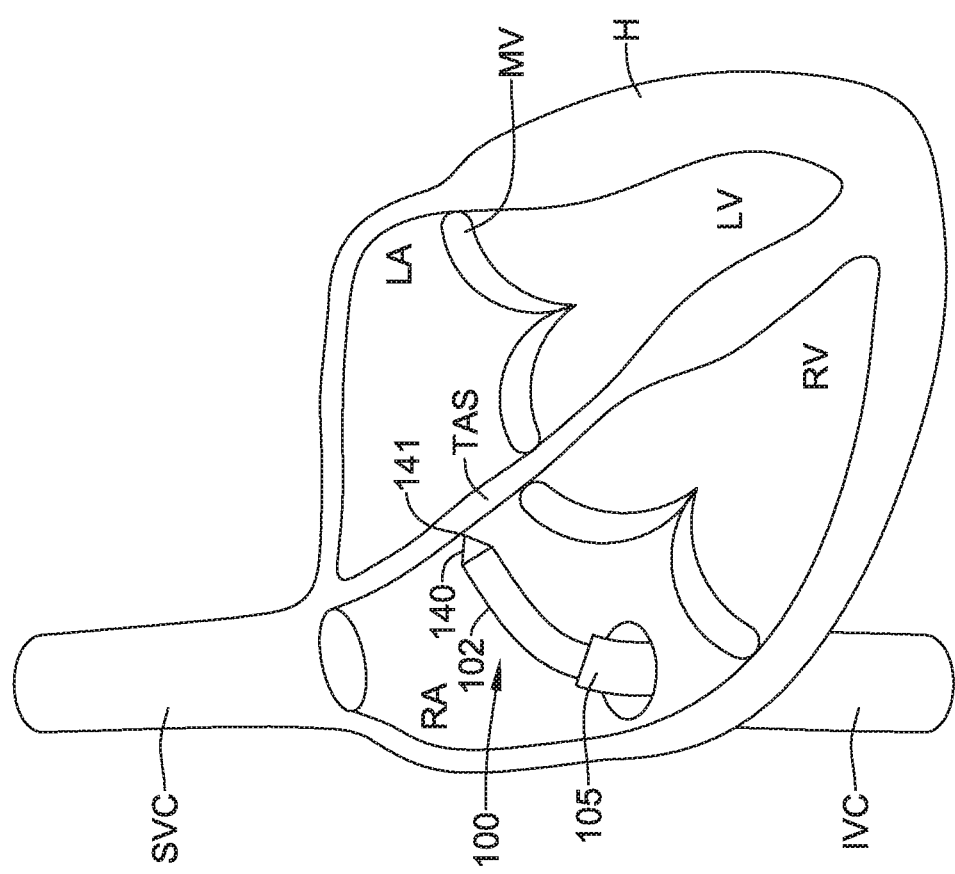
FIGS. 18A-18H are schematic views illustrating the use of the illustrative delivery device to deliver an implantable leadless cardiac pacing device.

Turning to FIG. 18A, the delivery device 100 may be advanced through vasculature of a patient and into the right atrium RA of the patient's heart H. As shown in FIG. 18A, the delivery device 100 may be advanced through the vasculature of a patient via a femoral approach and arrive at the right atrium RA through intra vena cava IVC. Alternatively, the delivery device 100 may be advanced through the vasculature of a patient via a jugular approach and arrive at the right atrium RA through the superior vena cava SVC. Other approaches may be utilized, as desired.

As shown in FIG. 18A, a guide catheter or introducer 105 has been inserted into the right atrium RA. Although not illustrated, the guide catheter or introducer 105 may be inserted into the right atrium RA over a guide wire or otherwise inserted into the right atrium RA prior to delivering the delivery device 100 to the right atrium RA. Then, once a distal end of the guide catheter or introducer 105 is inserted into the right atrium RA, the delivery device 100 may be passed there through and delivered to the right atrium RA.

Figure 18B:
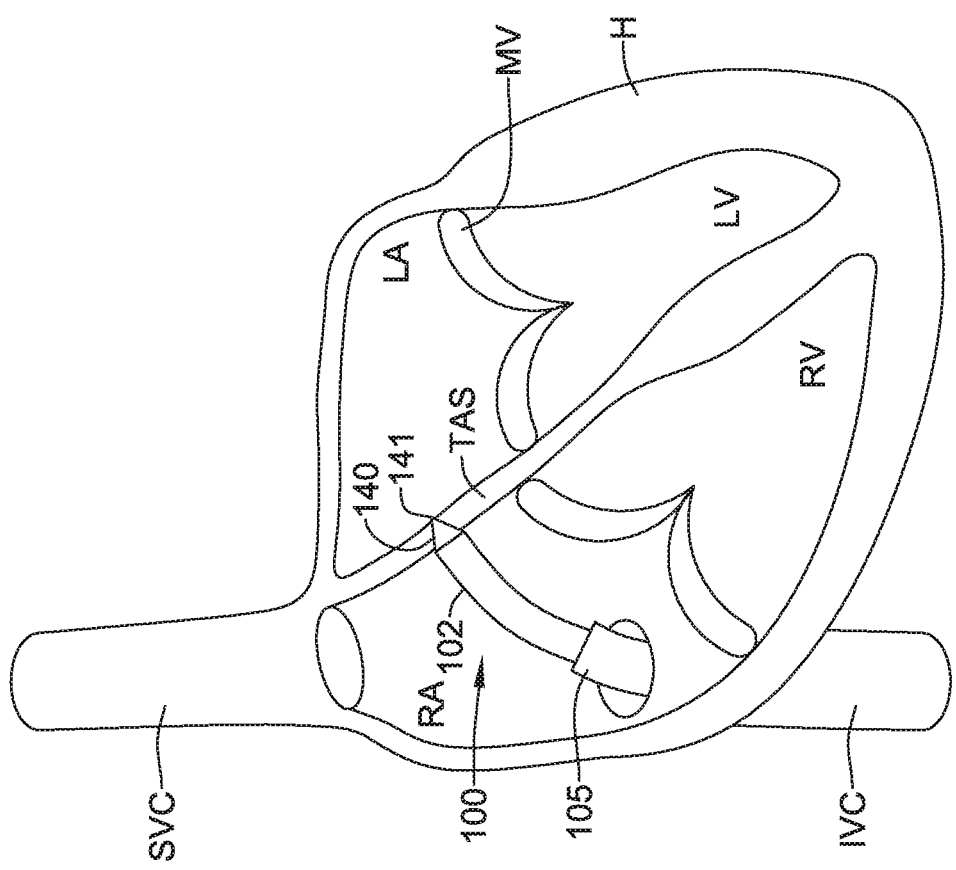

Once the distal end of the delivery device 100 (e.g., a portion of the outer tubular member, the tubular member 110, the distal holding section 108, and the distal tip portion 140) is located in the right atrium RA, the penetrating tip 141 of the distal tip portion 140 may be advance to and may engage the trans-atrial septum TAS. In one example, the penetrating tip 141 may engage the trans-atrial septum TAS at the fossa ovalis, which is a depression in the trans-atrial septum TAS that may be a thin fibrous material covering the foramen ovale. When engaging the trans-atrial septum TAS, the penetrating tip 141 may provide an initial puncture of the trans-atrial septum TAS. In one alternative, a needle or wire may provide an initial puncture of the trans-atrial septum TAS prior to or after advancing the delivery device 100 to the right atrium RA. In such cases, the delivery device 100 may include a side port (e.g., lumen 146 or lumen 158) for threading a needle or wire there through to the trans-atrial septum TAS and establishing an initial puncture. In one alternative, a needle or wire may be passed through the guide catheter or introducer 105 to the trans-atrial septum TAS Once the penetrating tip 141 has engaged the trans-atrial septum TAS, with the distal tip portion 140 in the closed penetrating position, the distal tip portion 140 may be advanced at least partially through the trans-atrial septum TAS until the penetrating tip 141 extends through or nearly extends through the trans-atrial septum TAS, as shown in FIG. 18B. The distal tip portion 140 may dilate the opening in the trans-atrial septum TAS caused by the initial puncture as it is advanced through the trans-atrial septum TAS such that the outer tubular member 102 may be able to cross the trans-atrial septum. Alternatively or additionally, actuation of the distal tip portion 140 while the distal tip portion 140 is in the trans-atrial septum TAS may dilate the opening in the trans-atrial septum TAS, such that the delivery device 100 carrying the implantable leadless pacing device 10 may cross the trans-atrial septum TAS. The distal tip portion 140 may be actuated with any passive or active actuation mechanism discussed herein or otherwise. In one example, the distal tip portion 140 may be actuated from the closed penetrating position to the opened position by advancing the implantable leadless pacing device 10 within the distal holding section 108 to engage the implantable leadless pacing device 10 with an inner surface of the distal tip portion 140, as discussed for example with respect to FIGS. 7A, 7B, 11A, and 11B.

Figure 18C:
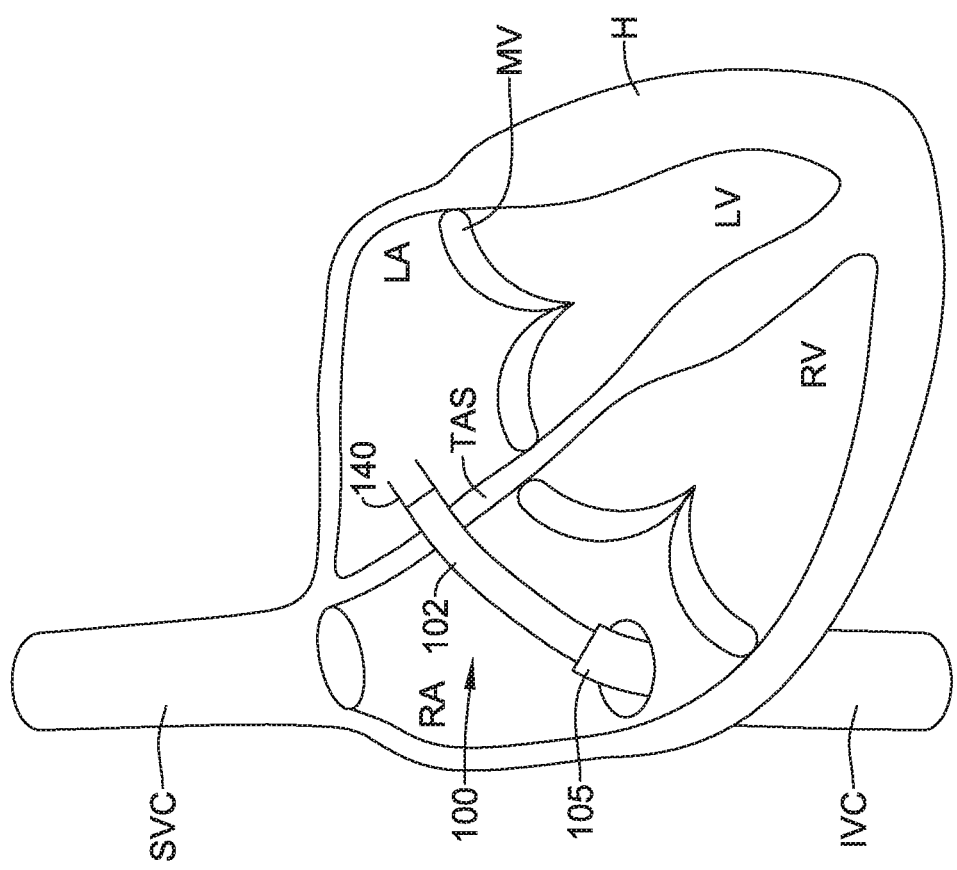
Figure 18D:
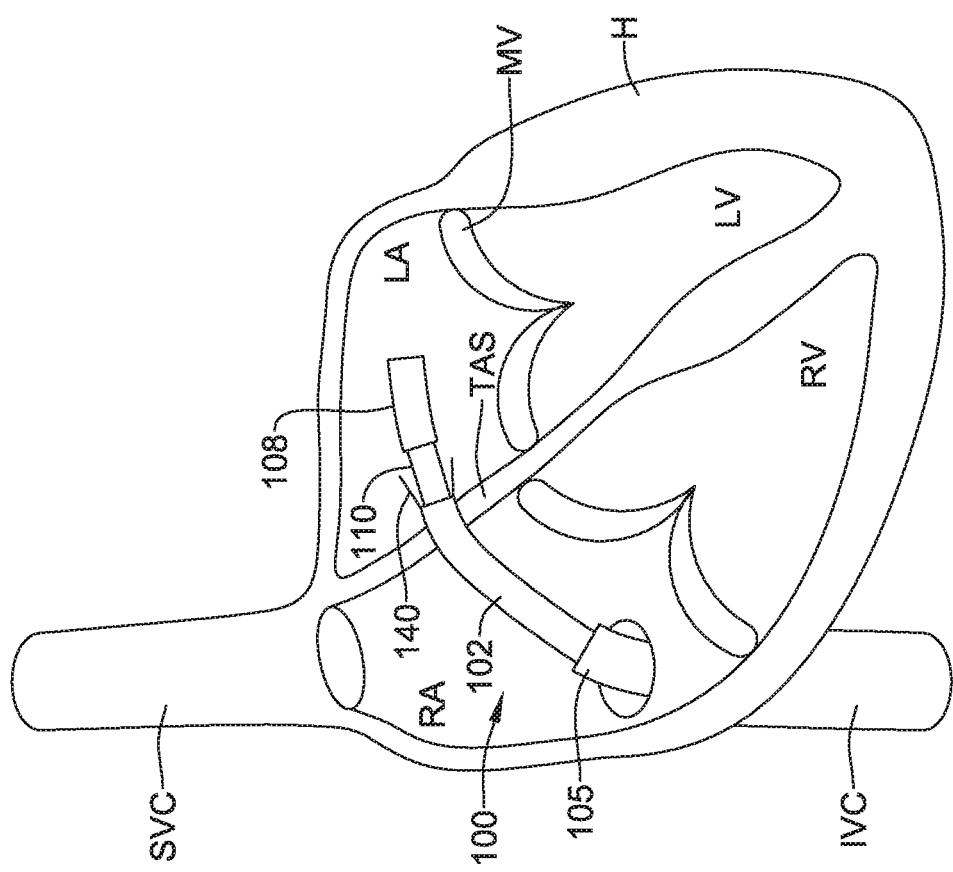

As shown in FIG. 18C, once the opening through the trans-atrial septum TAS has been dilated, the outer tubular member 102 may be advanced into the left atrium LA of the patient's heart H and the distal tip portion 140 may be opened if it has not already been opened, but this is not required. Once the outer tubular member 102 is located in the left atrium LA and the distal tip portion 140 is actuated to an opened position, the distal holding section 108 and the tubular member 110 may be advanced distally of a distal end of the outer tubular member 102 and the distal tip portion 140, as shown in FIG. 18D.

This method of crossing the trans-atrial septum TAS may result in less trauma to a patient, reduced procedure times, reduced opportunities for operator error, and/or other benefits as a result of not having to remove a dilator for dilating an opening through the trans-atrial septum TAS from a patient's vasculature prior to advancing the distal holding section 108 across the trans-atrial septum TAS. This technique may be termed a single stage method of delivering an implantable leadless pacing device 10 to a target area, as only a single pass is required to dilate and cross the trans-atrial septum TAS with the implantable leadless pacing device 10.

Figure 18E:
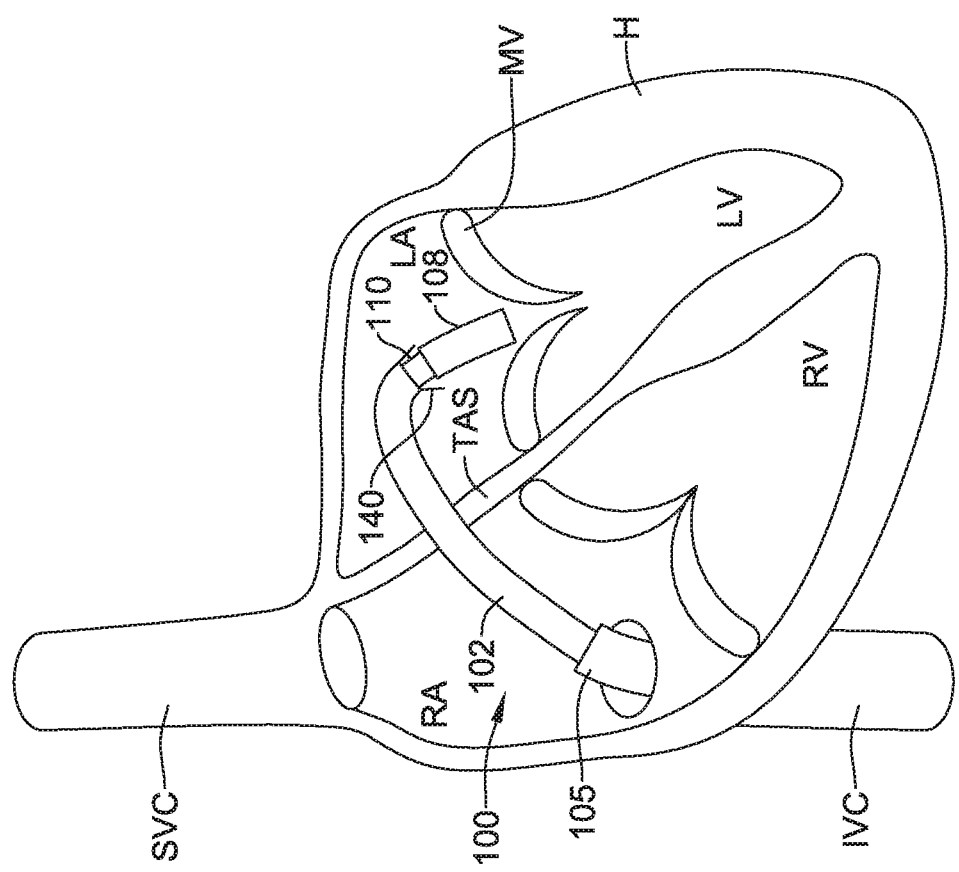
Figure 18F:
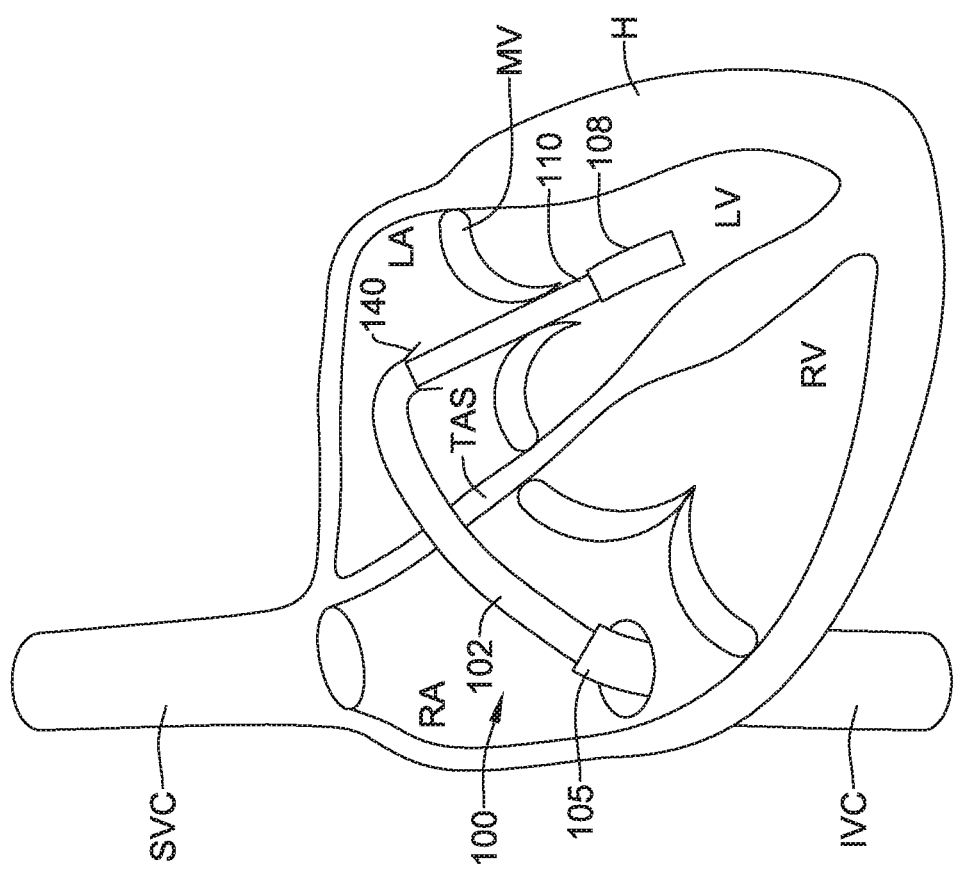

If the target location is in the left ventricle LV, a torque may be applied to a distal end of the outer tubular member 102 once the distal tip portion 140, the distal holding section 108, the tubular member 110, the outer tubular member 102, and if present, the implantable leadless pacing device 10 are in the left atrium LA. In some cases, the torque may be applied to the distal end of the outer tubular member 102 by actuating (e.g., rotating) the external rotatable member 124 (e.g., a first actuatable member) in communication with the outer tubular member 102 to deflect the distal end of the outer tubular member 102, the distal holding section 108, and the distal tip portion 140 in a radial direction toward the left ventricle LV, as shown in FIG. 18E. Once the outer tubular member 102 has been deflected in a radial direction toward the left ventricle, the distal holding section 108, the tubular member 110, and if present, the implantable leadless pacing device 10 may be advanced through a mitral valve MV of the heart H and into the left ventricle LV, as shown in FIG. 18F.

Figure 18G:
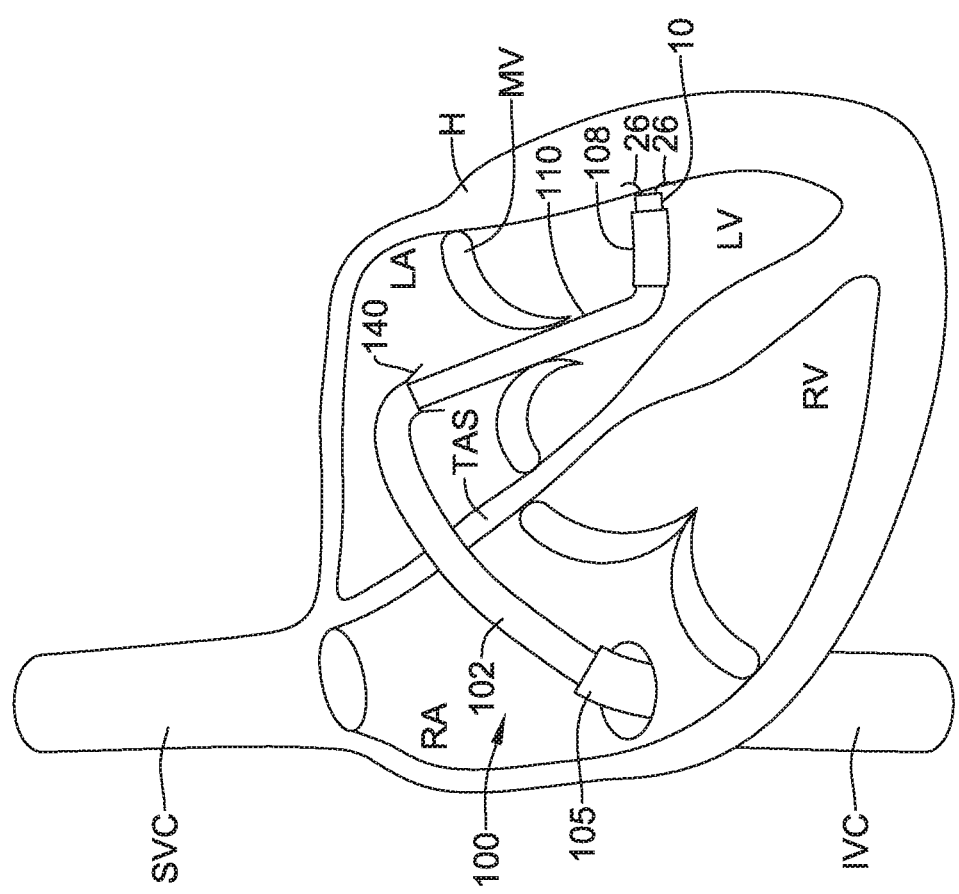
Figure 18H:
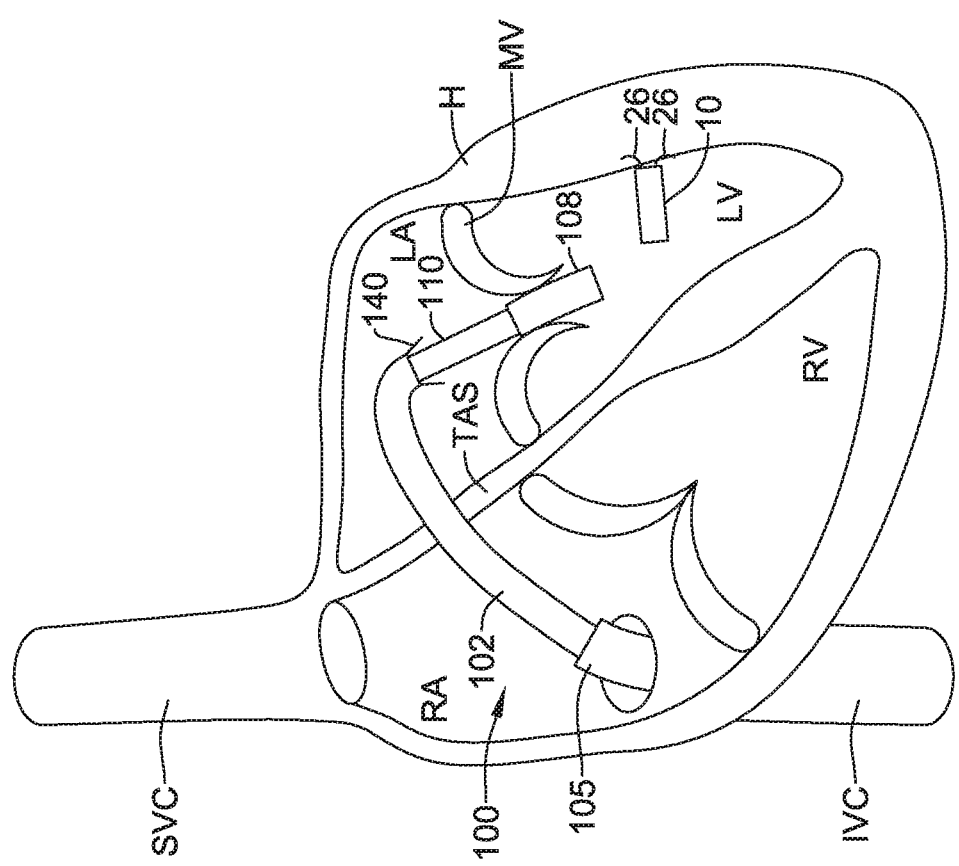

As shown in FIG. 18G, a torque may be applied to a distal end of the tubular member 110 once the distal holding section 108, the tubular member 110, and if present, the implantable leadless pacing device 10 are in the left ventricle LV. In some cases, the torque may be applied to the distal end of the tubular member 110 by actuating the external rotatable member 129 (e.g., a second actuatable member) in communication with the tubular member 110 to deflect the distal end of the tubular member 110 and the distal holding section 108 in a radial direction and toward a target location for implanting the implantable leadless pacing device 10 (or toward a location of an already implanted leadless pacing device for retrieval or other procedure). Once the tubular member 110 has been deflected in a radial direction toward the target location, the implantable leadless pacing device may be advanced out of the distal holding section 108 and into contact with wall of the left ventricle such that the hooks or tines 26 may engage the heart wall. Once the implantable leadless pacing device 10 has been implanted in (or captured from) the left ventricle, the delivery device 100 may be withdrawn, as started in FIG. 15H, through the heart H and vasculature of the patient in a manner similar to the delivery device 100 was inserted.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100 and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A trans-septal delivery device for delivering an implantable leadless pacing device, the delivery device comprising:

a tubular member including a lumen extending from a proximal end to a distal end thereof;

a distal holding section fixed to and extending distally of a distal end of the tubular member, the distal holding section defining a cavity therein for receiving an implantable leadless pacing device, the distal holding section having an outer diameter greater than an outer diameter of the tubular member;

a penetrating tip member actuatable from a closed penetrating position to an opened position, the penetrating tip member extending distally of a distal end of the distal holding section, the penetrating tip member configured to allow the implantable leadless pacing device to be deployed through the penetrating tip member when in the opened position;

an inner member elongated from a proximal end to a distal end thereof, the inner member slidably disposed within the lumen of the tubular member; and a handle assembly attached to the tubular member and the inner member.

2. The trans-septal delivery device of claim 1, wherein the penetrating tip member is secured relative to a distal end region of the tubular member.

3. The trans-septal delivery device of claim 1, wherein:
the handle assembly includes a first hub portion affixed adjacent to the proximal end of the tubular member and a second hub portion affixed adjacent to the proximal end of the inner member; and
the second hub portion is adjustable relative to the first hub portion to adjust a longitudinal position of the inner member relative to the tubular member.

4. The trans-septal delivery device of claim 1, wherein longitudinal movement of the inner member in a first direction relative to the tubular member actuates the penetrating tip member from the closed penetrating position to the opened position.

5. The trans-septal delivery device of claim 4, wherein longitudinal movement of the inner member in a second direction relative to the tubular member actuates the penetrating tip member from the opened position to the closed penetrating position.

6. The trans-septal delivery device of claim 1, wherein the penetrating tip member includes electrically activated polymer, the electrically activated polymer is activated to actuate the penetrating tip member from the closed penetrating position to an opened position.

7. The trans-septal delivery device of claim 1, further comprising:
a balloon in communication with the penetrating tip member; and
wherein the balloon is actuated to actuate the penetrating tip member from the closed penetrating position to the opened position.

8. The trans-septal delivery device of claim 1, wherein:
the penetrating tip member comprises a plurality of plate members; and
each plate member has a first end attached to the distal holding section of the tubular member and a second free end.

9. The trans-septal delivery device of claim 1, wherein the penetrating tip member comprises an adjustable wire and a polymer material covering the adjustable wire, wherein the adjustable wire is a spiral spring.

10. The trans-septal delivery device of claim 1, further comprising:
an outer tubular member including a lumen extending from a proximal end to a distal end thereof, the lumen of the outer tubular member slidably receives the tubular member.

11. The trans-septal delivery device of claim 10, wherein the penetrating tip member is secured relative to a distal end region of the outer tubular member.

12. The trans-septal delivery device of claim 11, wherein the distal holding section is positionable in the lumen of the outer tubular member and advanceable distally from the outer tubular member through the penetrating tip member.

13. The trans-septal delivery device of claim 1, wherein the penetrating tip member is secured to the distal end of the distal holding section.

14. The trans-septal delivery device of claim 1, further comprising:
an outer tubular member including a lumen extending from a proximal end to a distal end thereof;
wherein the tubular member is slidably disposed within the lumen of the outer tubular member; and
wherein the distal holding section and the penetrating tip member are both positioned distal of the distal end of the outer tubular member with the penetrating tip member in the closed penetrating position.

15. The trans-septal delivery system of claim 14, wherein the handle assembly includes:
a first hub portion affixed to the proximal end of the tubular member,
a second hub portion affixed to the proximal end of the inner member; and
a third hub portion affixed to the proximal end of the outer tubular member.

16. The trans-septal delivery system of claim 15, wherein the handle assembly further comprises a first actuation member actuatable to deflect a distal end region of the outer tubular member into an arcuate bend.

17. A trans-septal delivery device for delivering an implantable leadless pacing device, the delivery device comprising:
a tubular member including a lumen extending from a proximal end to a distal end thereof;
a distal holding section extending distally of a distal end of the tubular member, the distal holding section defining a cavity therein for receiving an implantable leadless pacing device;
a penetrating tip member actuatable from a closed penetrating position to an opened position, the penetrating tip member extending distally of a distal end of the distal holding section;
an inner member elongated from a proximal end to a distal end thereof, the inner member slidably disposed within the lumen of the tubular member;
a handle assembly attached to the tubular member and the inner member; and
a penetrating device extending distally of the penetrating tip member;
wherein the penetrating device has a sharp distal end configured to engage a trans-atrial septum and create an initial opening through which the penetrating tip member is inserted.

18. A trans-septal delivery system for delivering an implantable leadless pacing device, the system comprising:
a delivery device comprising:
an outer tubular member including a lumen extending from a proximal end to a distal end thereof;
a tubular member including a lumen extending from a proximal end to a distal end thereof, the tubular member slidably disposed within the lumen of the outer tubular member;
a distal holding section extending distally of a distal end of the tubular member, the distal holding section defining a cavity therein;
a penetrating tip member actuatable from a closed penetrating position to an opened position, the penetrating tip member extending distally of a distal end of the distal holding section; and
an implantable leadless pacing device disposed within the cavity of the distal holding section;
wherein the penetrating tip member is configured to allow the implantable leadless pacing device to be deployed through the penetrating tip member when in the opened position.

19. The trans-septal delivery device of claim 18, wherein the penetrating tip member is secured relative to a distal end region of the outer tubular member.

20. The trans-septal delivery device of claim 18, wherein the penetrating tip member is secured relative to a distal end region of the tubular member.

\* \* \* \* \*